US008465761B2

(12) United States Patent
Navarro et al.

(10) Patent No.: US 8,465,761 B2
(45) Date of Patent: Jun. 18, 2013

(54) PIGLET FEED RATIONS HAVING LOW LEVELS OF FERMENTABLE CARBOHYDRATES

(75) Inventors: Felipe Navarro, O'Fallon, MO (US); Robert John Harrell, Troy, MO (US); Bradley V. Lawrence, Plattsburg, MO (US); Randy L. Anderson, Stauton, IL (US)

(73) Assignee: Novus International, Inc., St. Charles, MO (US)

( * ) Notice: Subject to any disclaimer, the term of this patent is extended or adjusted under 35 U.S.C. 154(b) by 470 days.

(21) Appl. No.: 12/667,355

(22) PCT Filed: Jul. 1, 2008

(86) PCT No.: PCT/US2008/068915
§ 371 (c)(1),
(2), (4) Date: Apr. 1, 2010

(87) PCT Pub. No.: WO2009/006475
PCT Pub. Date: Jan. 8, 2009

(65) Prior Publication Data
US 2011/0008388 A1    Jan. 13, 2011

Related U.S. Application Data

(60) Provisional application No. 60/947,817, filed on Jul. 3, 2007.

(51) Int. Cl.
*A23K 1/18* (2006.01)
(52) U.S. Cl.
USPC ............ 424/442; 424/93.51; 426/2; 426/658; 514/53

(58) Field of Classification Search
USPC ........................................................ 424/442
See application file for complete search history.

(56) References Cited

U.S. PATENT DOCUMENTS

| 2,938,053 | A | 5/1960 | Blake |
| 4,027,043 | A | 5/1977 | Schroeder |
| 4,460,588 | A | 7/1984 | Serban |
| 4,642,317 | A | 2/1987 | Palmquist |
| 4,762,854 | A | 8/1988 | Lloyd |
| 4,820,527 | A | 4/1989 | Christensen |

(Continued)

FOREIGN PATENT DOCUMENTS

| CA | 1261855 | 9/1989 |
| EP | 0937706 | 8/1999 |

(Continued)

OTHER PUBLICATIONS

Mroz, "Supplementary organic acids and their interactive effects with microbial phytase in diets for pigs and poultry", Proceedings, Annual Conference on Phytase in Animal Nutrition, 2000, pp. 1-25, Lublin, Poland.

(Continued)

*Primary Examiner* — Neil Levy
(74) *Attorney, Agent, or Firm* — Polsinelli Shughart PC

(57) ABSTRACT

The present invention provides compositions comprising at least one acidifying agent, at least one immune stimulating agent, at least one antioxidant, and optionally, at least one tissue regeneration agent. The compositions comprise premixes for inclusion in the diets of piglets, wherein the diets have low levels of fermentable carbohydrates.

8 Claims, 3 Drawing Sheets

U.S. PATENT DOCUMENTS

| | | | |
|---|---|---|---|
| 5,244,681 | A | 9/1993 | Vinci |
| 5,462,967 | A | 10/1995 | Hayashi |
| 5,591,467 | A | 1/1997 | Bland |
| 5,603,958 | A | 2/1997 | Morein |
| 5,698,244 | A | 12/1997 | Barclay |
| 5,795,602 | A | 8/1998 | Craig |
| 5,891,491 | A | 4/1999 | Owens |
| 5,928,686 | A | 7/1999 | Ivey |
| 5,945,144 | A | 8/1999 | Hahn |
| 5,985,336 | A | 11/1999 | Ivey |
| 6,008,409 | A | 12/1999 | Hasseberg |
| 6,017,564 | A | 1/2000 | Owens |
| 6,210,718 | B1 | 4/2001 | Ivey |
| 6,355,289 | B1 | 3/2002 | Rolow |
| 6,436,453 | B1 | 8/2002 | Van Lengerich |
| 6,593,283 | B2 | 7/2003 | Hei |
| 6,841,181 | B2 | 1/2005 | Jager |
| 6,846,478 | B1 | 1/2005 | Doyle |
| 6,955,831 | B2 | 10/2005 | Higgs |
| 7,258,880 | B2 | 8/2007 | Piva |
| 2002/0172737 | A1 | 11/2002 | Pinski |
| 2003/0077254 | A1 | 4/2003 | Ramaekers |
| 2003/0162809 | A1 | 8/2003 | Selm |
| 2003/0176500 | A1 | 9/2003 | Molly |
| 2004/0009206 | A1 | 1/2004 | Piva |
| 2004/0028732 | A1 | 2/2004 | Falkenhausen |
| 2004/0076659 | A1 | 4/2004 | Shelford |
| 2004/0115275 | A1 | 6/2004 | Tsou |
| 2004/0156816 | A1 | 8/2004 | Anderson |
| 2004/0175434 | A1 | 9/2004 | Schasteen |
| 2005/0019461 | A1 | 1/2005 | Cazemier |
| 2005/0100563 | A1 | 5/2005 | Hexamer |
| 2006/0018847 | A1 | 1/2006 | Kroepke |
| 2006/0251633 | A1 | 11/2006 | Salvadori |
| 2007/0048432 | A1* | 3/2007 | Holzgraefe et al. .......... 426/658 |
| 2007/0118916 | A1 | 5/2007 | Puzio |

FOREIGN PATENT DOCUMENTS

| | | |
|---|---|---|
| EP | 1062879 A1 | 12/2000 |
| JP | 08107757 | 4/1996 |
| JP | 10327751 | 12/1998 |
| JP | 03107789 B | 11/2000 |
| JP | 03270588 B | 4/2002 |
| WO | 9635337 | 11/1996 |
| WO | 9733488 | 9/1997 |
| WO | 9904646 | 2/1999 |
| WO | 0059877 | 10/2000 |
| WO | 0197799 | 12/2001 |
| WO | 03037103 | 5/2003 |
| WO | 03084346 | 10/2003 |

OTHER PUBLICATIONS

Nitsan, "Growth and development of the digestive organs and some enzymes in broiler chicks after hatching", British Poultry Science, Jul. 1991, pp. 515-523, vol. 32, No. 3.

Nitsan, "The effects of force-feeding on enzymes of the liver, kidney, pancreas and digestive tract of chicks", The British Journal of Nutrition, Sep. 1974, pp. 241-247, vol. 32, No. 2, Cambridge University Press, England.

Partanen, "Organic acids—their efficacy and modes of action in pigs", Gut Environment of Pigs, 2001, pp. 201, Nottingham University Press, Nottingham, UK.

Partanen, "Organic acids for performance enhancement in pig diets", Nutr. Res. Rev., 1999, pp. 117-145, vol. 12.

Roura, "Prevention of Immunologic Stress Contributes to the Growth-Permitting Ability of Dietary Antibiotics in Chicks", The Journal of Nutrition, 1992, pp. 2383-2390, vol. 122, Wistar Institute of Anatomy and Biology, Philadelphia.

Smulders, "Effect of antimicrobial growth promoter in feeds with different levels of undigestible protein on broiler performance", Proceedings, World's Poultry Sci. Meeting, Aug. 1999, pp. 177-179, Veldhoven, Netherlands.

Thaela, "Effect of lactic acid supplementation in pigs after weaning", Journal of Animal and Feed Science, 1998, pp. 181, vol. 7.

Thomlinson, "Dietary manipulation of gastric pH in the prophylaxis of eneteric disease in weaned pigs: Some field observations", The Veterinary Record, Aug. 1981, pp. 120-122, vol. 109, British Veterinary Associate, London.

Visek, "The mode of growth promotion by antibiotics", Journal of Animal Science, Apr. 1978, pp. 1447-1469, vol. 46, No. 5, American Society of Animal Science.

Doerr, Possible anti-fungal effects of hydroxy-methylthio-butanoic acid (HMB), Poultry Science, 1995, vol. 74(1), pp. 23—Abstract Only.

International Search Report for PCT/US07/72436 dated Dec. 18, 2007; 9 pgs.

Van NeVel, "Determination of rumen microbial growth in vitro from P-labelled phosphate incorporation", British Journal of Nutrition, 1977, vol. 38, pp. 101-114.

Dunkley, "Supplementing Rations with Tocopherol and Ethoxyquin to Increase Oxidative Stability", J. Dairy Sci., 1967, vol. 50, No. 4, pp. 492-499.

Dunkley, "Compounds in Milk Accompanying Feeding of Ethoxyquin", J. Dairy Sci., 1968, vol. 51, No. 8, pp. 1215-1218.

Han, "Carbohydrate fermentation and nitrogen metabolism of a finishing beef diet by ruminal microbes in continuous cultures as affected by ethoxyquin and(or) supplementation of monensin and tylosin", J. Anim. Sci., 2002, vol. 80, pp. 1117-1123.

English Translation of Chinese Office action from related Application No. 200780047219.5 received from foreign associate on Oct. 21, 2011, 7 pgs.

International Search Report and Written Opinion dated Sep. 30, 2008 from related International application No. PCT/US08/68915, 8 pgs.

Fatty acid composition of some common edible fats and oils Zamora (2005) http://www.scientificpsychic.com/fitness/fattyacids1.html.

Boles, "Effects of Barley Variety Fed to Steers on Carcass Characteristics and Color of Meat", Journal of Animal Science, 2004, vol. 82, pp. 2087-2091.

Osman, "Oil Content and Fatty Acid Composition of Some Varieties of Barley and Sorghum Grains", 2000, vol. 51, Fasc. 3, pp. 157-162.

Gauthier, "Organic Acids and Essential Oils, A Realistic Alternative to Antibiotic Growth Promoters in Poultry", Forum Internancional de Avicultura 17 a 19 de Agosto de 2005, Foz do Iguacu, PR, Brasil, pp. 148-157.

International Search Report for PCT/US07/84497, dated Sep. 24, 2008; 5 pgs.

Supplementary European Search Report for EP 07 87 1446, dated Nov. 18, 2009; 2 pgs.

Baur, "The Fatty Acids of Corn Oil", Journal of the American Chemical Society, 1945, 67:1899-1900.

Afzalpurkar, "Variation in Oil Content and Fatty Acid Composition with Sunflower Head Size and Shape", Journal of the American Oil Chemists' Society, 1980, 57:105-106.

Burns, "Sulfur Amino Acid Requirements of immature Beagle Dogs", Journal of Nutrition, 2981, vol. 111, No. 12, pp. 2117-2124, Dec. 1981.

Cha, "Identification of Aroma-Active Compounds in Korean Salt-Fermented Fishes by Aroma Extract Dilution Analysis" Korean Society of Food Science and Nutrition, 1999, vol. 28, No. 2, pp. 312-318—Abstract Only.

Martin, "The Effect of Tuber Composition on Potato Crisp Flavour", Department of Food Science & Technology, University of Reading, proceedings of the Weuman Flavour Research Symposium, Germany, Jun. 22-25, 1999, Chemical Abstracts, Database No. 136:69008—Abstract Only.

Robinson, "Influence of Abomasal Infusion of High Levels of Lysine or Methionine, or Both, on Ruminal Fermentation, Eating Behaviour and Performance of Lactating Dairy Cows", Journal of Animal Science, 2000, vol. 78, No. 4, pp. 1067-1077—Abstract Only.

Smit, "Flavour Formation by Enzymatic Conversion of Amino Acids", Proceedings of the Weurman Flavour Research Symposium, Germany, Jun. 22-25, 1999, Chemical Abstracts, Database No. 136:84940—Abstract Only.

Lamikanra, "Biochemical and Microbial Changes during the Storage of Minimally Processed Cantaloupe", Journal of Agricultural and Food Chemistry, 2000, vol. 48(12), Abstract, American Chemical Society.

Ozer, "Effect of addition of amino acids, treatment with .beta.-galactosidase and use of heat-shocked cultures on the acetaldehyde level in yoghurt", International Journal of Dairy Technology, 2002, vol. 55(4), Abstract, Blackwell Science Ltd.

Anderson, "Gut microbiology and growth-promoting antibiotics in swine", Pig News and Information, 1999, pp. 115N-122N, vol. 20, No. 4, CABI Publishing, Farnham Royal, England.

BASF Fine Chemicals, "Effect of Luprosil(R) NC applications to litter on the health and performance of turkeys", 1990, BASF Technical Bulletin KC 9037.

Bedford, "Removal of antibiotic growth promoters from poultry diets: implications and strategies to minimise subsequent problems", World's Poultry Science Journal, Dec. 2000, pp. 347-365, vol. 56.

Bone, "The production of urinary phenols by gut bacteria and their possible role in the causation of large bowel cancer", The American Journal of Climincal Nutrition, Dec. 1976, pp. 1448-1454, vol. 29, No. 12.

Botermans, "The exocrine pancreas in pig growth and performance", Biology of the Pancreas in Growing Animals, 1999, pp. 395-408, Elsevier Science.

Brachet, "Transport of Methionine Hydroxy Analog across the Brush Border Membrane of Rat Jejunum", The Journal of Nutrition, 1987, pp. 1241-1246, vol. 117, wistar Institute of Anatomy and Biology, Philadelphia.

Chaveerach, "In Vitro Study on the Effect of Organic Acids on Campylobacter jejuni/coli Populations in Mixtures of Water and Feed", Poultry Science, May 2002, pp. 621-628, vol. 81, No. 5.

Cherrington, "Organic Acids: Chemistry, Antibacterial Activity and Practical Applications", Advances in Microbial Physiology, 1991, pp. 87-108, vol. 32.

Coates, "The Effect of Antibiotics on the Intestine of the Chick", The British Journal of Nutrition, 1995, pp. 110-119, vol. 9, No. 1, Cambridge University Press, Cambridge, England.

Cole, "The Effect on Performance and Bacterial Flora of Lactic acid, Propionic acid, Calcium propionate and Calcium acrylate in the Drinking Water of Weaned Pigs", The Veterinary Record, Nov. 2, 1968, pp. 459-464, vol. 83, British Veterinary Association, London.

Corthier, "Interrelationships between Digestive Proteolytic Activities and Production and Quantitation of Toxins in Pseudomembranous colitis Induced by Clostridium difficile in Gnotobiotic Mice", Infection and Innunity, Dec. 1989, pp. 3922-3927, vol. 57, No. 12, American Society for Microbiology, Washington.

Cranwell, "Development of the Neonatal Gut and Enzyme Systems", The Neonatal Pig—Development and Survival, 1995, pp. 99-154, M.A. Varley, CAB International, Oxon.

Dierick, "Influence of the gut flora and of some growth promoting feed additives on nitrogen metabolism in pigs. I. Studies in vitro", Livestock Production Science, 1986, pp. 161-176, vol. 14, Elsevier Science Publishers, Amsterdam.

Dierick, "Influence of the gut flora and of some growth promoting feed additives on nitrogen metabolism in pigs. II Studies in vivo", Livestock Production Science, 1986, pp. 177-193, vol. 14, Elsevier Science Publishers, Amsterdam.

Dunnington, "Enzyme Activity and Organ Development in Newly Hatched Chicks Selected for High or Low Eight-Week Body Weight", Poultry Science, 1995, pp. 761-770, vol. 74, No. 5.

Eidelsburger, "Zum Einflub von Fumarsaure, Salzsaure, Natriumformiate, Tylosin und Toyocerin auf tagliche Zunahmen, Futteraufnagme, Futterverwertug und Verdaulichkeit", J. Anim. Physiol. A. Anim. Nutr., 1992, pp. 82-92, vol. 68.

Eidelsburger, "Zum Einflub von Ameisenaure, Calciumformiat und Natriumhydrogencarbonat auf pH-Wert, Trockenmassegehalt, Konzentration an Carbonsauren und Ammoniak in verschiedenen Segmenten des Gastrointestinaltraktes", J. Anim. Physiol. A. Anim. Nutri., 1992, pp. 30-32, vol. 68.

Engelhardt, "Absorption of Short-chain Fatty Acids and Their Role in the Hindgut of Monogastric Animals", Animal Feed Science and Technology, 1989, pp. 43-53, vol. 23, Elsevier Science Publishers, Amsterdam.

Enthoven, "Antibacterial properties of 2-hydroxy-4-(methylthio)butyric Acid HMB, alimet)", Eur. Assoc. Anim. Prod. Proc., 2002, EEAP, Cairo—Abstract Only.

Franti, "Antibiotic Growth Promotion: Effects of Zinc Bacitracin and Oxytetracycline on the Digestive, Circulatory, and Excretory Systems of New Hampshire Cockerels", Poultry Science, 1972, pp. 1137-1145, vol. 51, No. 4.

Gabert, "The effect of fumaric acid and sodium fumarate supplementation to diets for weanling pigs on amino acid digestibility and volatile fatty acid concentrations in ileal digesta", Animal Feed Science and Technology, 1995, pp. 243-254, vol. 53, Elsevier Science.

Gedek, "Zum Einflub von Fumarsaure, Salzsaure, Natriumformiat, Tylosin und Toyocerin auf die Keimzahlen der Mikroflora und deren Zusammensetzung in verschiedenen Segmenten des Gastrointestinaltraktes,", J. Anim. Physiol. A. Anim. Nutr., 1992, pp. 209-217, vol. 58.

Hadron, "Effect of different dosages of an organic-acid mixture in broiler diets", Archiv fuer Gefluegelkunde, 2001, pp. 22-27, vol. 65—Abstract Only.

Harada, "Effect of short-chain fatty acids on the secretory response of the ovine exocrine pancreas", American Journal of Physiology, Mar. 1983, pp. G284-G290, vol. 244, No. 3, The American Physiological Society.

Harada, "Postnatal development of biliary and pancreatic exocrine secretion in piglets", Comparative Biochemistry and Physiology, 1988, pp. 43-51, vol. 91A, No. 1, Pergamon Press, London.

Harada, "Comparison of Pancreatic Exocrine Secretion via Endogenous Secretin by Intestinal Infusion of Hydrochloric Acid and Monocarboxylic Acid in Anesthetized Piglets", Japanese Journal of Physiology, 1986, pp. 843-856, vol. 36, No. 5.

Huyghebaert, "The influence of the addition of 'organic acid'—preparations on the zootechnical performances of broiler chickens", Report: CLO-DVV, 1999.

Kato, "Effect of Short-Chain Fatty Acids on Pancreatic Exocrine Secretion in Calves Aged 2 Weeks and 13 Weeks", Japanese Veterinary Science, Dec. 1989, pp. 1123-1127, vol. 51, No. 6, Japanese Society of Veterinary Science.

Knight, "Comparative Absorption of 2-Hydroxy-4 (Methylthio) butanoic Acid and L-Methionine in the Broiler Chick", Journal of Nutrition, Nov. 1984, pp. 2179-2186, vol. 114, No. 11, Wiistar Institute of Anatomy and Biology, Philadelphia.

Makkink, "Acid binding capacity in feedstuffs", Feed International, Oct. 2001, pp. 24-27.

* cited by examiner

PIGLET FEED RATIONS HAVING LOW LEVELS OF FERMENTABLE CARBOHYDRATES

FIELD OF THE INVENTION

The present invention relates to compositions comprising pre-mixes for use in piglet diets having low levels of fermentable carbohydrates.

BACKGROUND OF THE INVENTION

Fermentable dietary carbohydrates make up roughly two-thirds of the young pig's diet and provide a valuable energy source. Unfortunately, ingredients rich in carbohydrates are expensive and, as such, their use dramatically impacts the cost of production. For example, the most utilized source of fermentable carbohydrate in piglet feeds immediately post weaning is lactose. In fact, lactose and ingredients with lactose have been shown to be beneficial in early nursery diets. Many producers feed lactose levels of approximately 20% in the first diet post weaning, and then reduce the level of lactose in subsequent post weaning diets. While lactose provides an excellent, easily digestible energy source, it may also facilitate the development of beneficial bacteria in the gastrointestinal tract of the piglet, such as *Lactobacilli*.

Because of the relatively high cost of lactose compared to other carbohydrate sources, a need exists for ingredients or combinations of ingredients that may be utilized in piglet feed rations to replace all or part of the lactose content without negatively impacting piglet health or performance.

SUMMARY OF THE INVENTION

Among the various aspects of the present invention is a provision for a composition comprising at least one acidifying agent, at least one immune stimulating agent, and at least one antioxidant.

Another aspect of the invention encompasses a method for transitioning a piglet from a weaning to a grower/finisher diet by feeding the piglet a ration comprising a low percentage of fermentable carbohydrate. The method comprises replacing at least about 50% of fermentable carbohydrate in a traditional Phase I or Phase II piglet feed ration with a composition comprising at least one acidifying agent, at least one immune stimulating agent, and at least one antioxidant, wherein the replacement of the fermentable carbohydrate does not substantially impact the piglet's performance.

A further aspect of the invention provides a piglet feed ration. The feed ration comprises a grain source, a crude protein source, a crude fat source, and a composition comprising at least one acidifying agent, at least one immune stimulating agent, at least one antioxidant, and at least one tissue regeneration agent.

Still another aspect of the invention encompasses a powdered milk replacer. The milk replacer comprises a crude protein source, a crude fat source, and a composition comprising at least one acidifying agent, at least one immune stimulating agent, at least one antioxidant, and at least one tissue regeneration agent.

Other aspects and feature of the invention will be in part apparent and in part pointed out hereinafter.

DETAILED DESCRIPTION OF THE INVENTION

Figure 1:
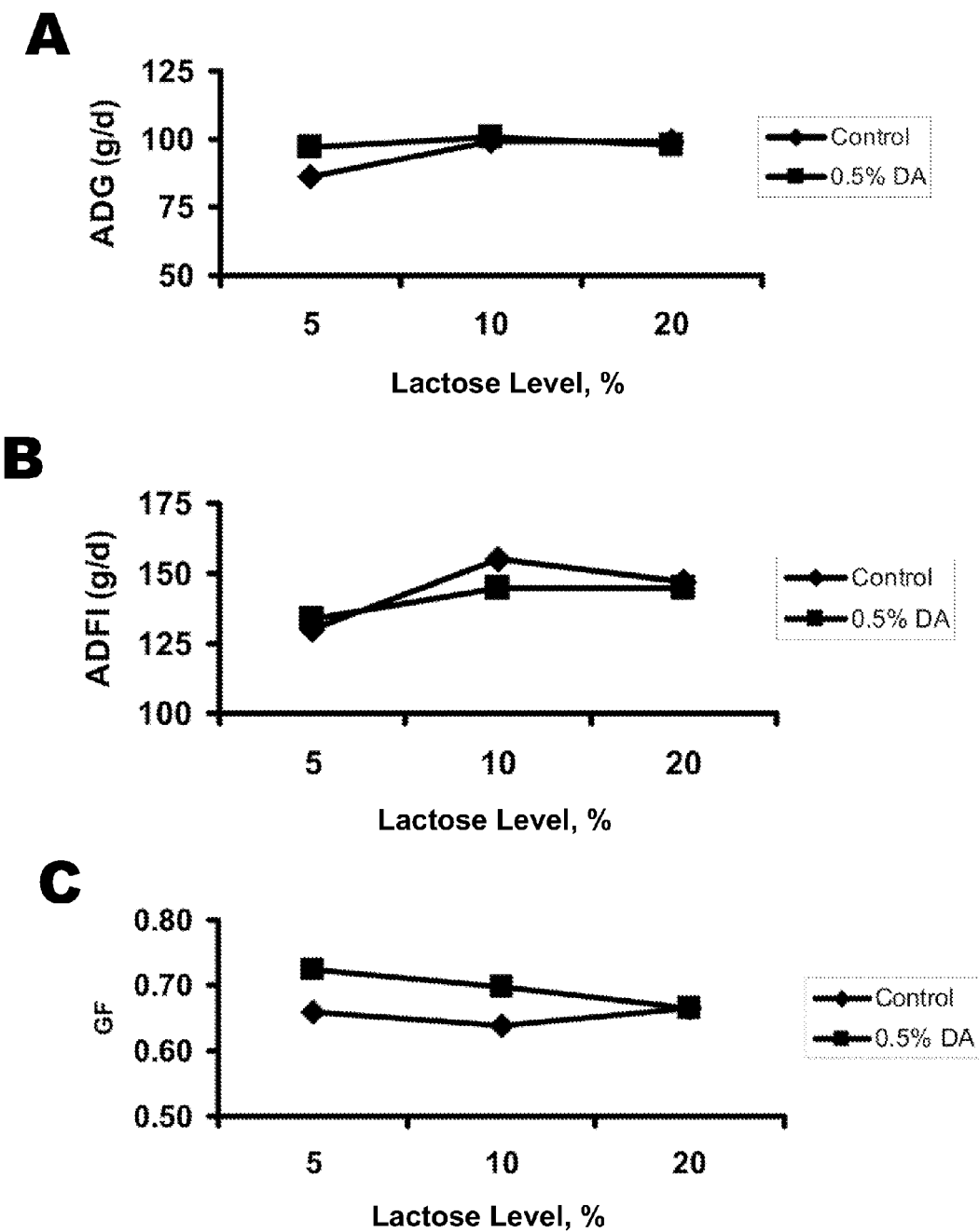
FIG. 1 graphically illustrates the effects of the level of lactose and an acidifying agent (DA) in nursery pig diets during Phase I (0 days to 10 days post weaning). Panel A presents the average daily weight gain (ADG) as a function of lactose level for the control and DA-treated groups. Panel B presents the average daily feed intake (ADFI) as a function of lactose level for the control and DA-treated groups. Panel C presents the gain to feed ratio (GF) as a function of lactose level for the control and DA-treated groups.

The compositions of the invention comprise pre-mixes that may be utilized in piglet feed rations to provide rations having low levels of fermentable carbohydrates, as described in more detail in section (II) below. Alternatively, the pre-mixes may be utilized in milk replacers to provide replacers having low levels of fermentable carbohydrates. As illustrated in the examples, the pre-mix compositions may be used to replace lactose in piglet feed rations without negatively impacting piglet health or performance.

(I) Pre-Mix Compositions

The pre-mix composition comprises at least one acidifying agent, an immune stimulating agent, at least one antioxidant, and optionally, a tissue regeneration agent. Each of the ingredients comprising the pre-mix composition is detailed below.

(a) Acidifying Agent

The premix composition includes at least one acidifying agent that is an organic acid. A variety of suitable organic acids may be utilized in the compositions of the invention. Suitable organic acids may be selected from the aliphatic, cycloaliphatic, aromatic, heterocyclic, carboxylic and sulfonic classes of organic acids. The organic acid may be selected from small monocarboxylic, dicarboxylic or tricarboxylic acids, or any active derivative or salt thereof. The organic acid may be a monocarboxylic acid having a straight chain or it may be branched; it may be saturated or unsaturated.

A variety of organic acids comprised of carboxylic acids are suitable. In one embodiment, the organic acid may contain from about two to about twenty-five carbon atoms. In another embodiment, the organic acid may have from about three to about twenty-two carbon atoms. In a further embodiment, the organic acid may contain from about three to about twelve carbon atoms. In yet another embodiment, the organic acid may contain from about eight to about twelve carbon atoms. In still another embodiment, the organic acid may contain from about two to about six carbon atoms. Suitable organic acids, by way of non-limiting example, include formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, and glutaric acid.

Salts of organic acids comprising carboxylic acids are also suitable for certain embodiments. Representative suitable salts include the ammonium, magnesium, calcium, lithium, sodium, potassium, selenium, iron, copper, and zinc salts of organic acids. In one embodiment, the organic acid is an ammonium, magnesium, calcium, lithium, sodium, potassium, selenium, iron, copper, or zinc salt of formic acid. In another embodiment, the organic acid is an ammonium, magnesium, calcium, lithium, sodium, potassium, selenium, iron, copper, or zinc salt of acetic acid. In yet another embodiment, the organic acid is an ammonium, magnesium, calcium, lithium, sodium, potassium, selenium, iron, copper, or zinc salt of propionic acid. In an additional embodiment, the organic acid is an ammonium, magnesium, calcium, lithium, sodium, potassium, selenium, iron, copper, or zinc salt of butanoic acid. In a further embodiment, the organic acid is an ammonium, magnesium, calcium, lithium, sodium, potassium, selenium, iron, copper, or zinc salt of benzoic acid. In still another embodiment, the organic acid is an ammonium, magnesium, calcium, lithium, sodium, potassium, selenium, iron, copper, or zinc salt of lactic acid. In yet another embodiment, the organic acid is an ammonium, magnesium, calcium, lithium, sodium, potassium, selenium, iron, copper, or zinc salt of malic acid. In still another embodiment, the organic acid is an ammonium, magnesium, calcium, lithium, sodium, potassium, selenium, iron, copper, or zinc salt of tartaric acid. In a further embodiment, the organic acid is an ammonium, magnesium, calcium, lithium, sodium, potassium, selenium, iron, copper, or zinc salt of mandelic acid. In yet another embodiment, the organic acid is an ammonium, magnesium, calcium, lithium, sodium, potassium, selenium, iron, copper, or zinc salt of citric acid. In an additional embodiment, the organic acid is an ammonium, magnesium, calcium, lithium, sodium, potassium, selenium, iron, copper, or zinc salt of fumaric acid. In an additional embodiment, the organic acid is an ammonium, magnesium, calcium, lithium, sodium, potassium, selenium, iron, copper, or zinc salt of sorbic acid. In another embodiment, the organic acid is an ammonium, magnesium, calcium, lithium, sodium, potassium, selenium, iron, copper, or zinc salt of boric acid. In yet another embodiment, the organic acid is an ammonium, magnesium, calcium, lithium, sodium, potassium, selenium, iron, copper, or zinc salt of succinic acid. In another embodiment, the organic acid is an ammonium, magnesium, calcium, lithium, sodium, potassium, selenium, iron, copper, or zinc salt of adipic acid. In yet another embodiment, the organic acid is an ammonium, magnesium, calcium, lithium, sodium, potassium, selenium, iron, copper, or zinc salt of glycolic acid. In an additional embodiment, the organic acid is an ammonium, magnesium, calcium, lithium, sodium, potassium, selenium, iron, copper, or zinc salt of glutaric acid.

Alternatively, the organic acid may be comprised of a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxyl groups. A substituted carboxylic acid with a hydroxyl group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine. Salts of organic acids comprising substituted carboxylic acids are also suitable for certain embodiments. Representative suitable salts include the ammonium, magnesium, calcium, lithium, sodium, potassium, selenium, iron, copper, and zinc salts of organic acids comprising substituted carboxylic acids.

In yet another embodiment, the organic acid may be a compound having Formula (I):

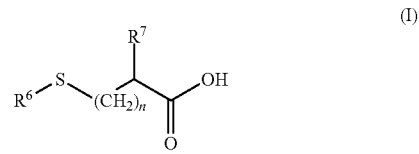

wherein:

n is an integer from 0 to 2;

$R^6$ is an alkyl group having from one to four carbon atoms;

$R^7$ is selected from the group consisting of hydroxyl, amino, and —$OCOR^8$ or —$NHCOR^8$; and $R^8$ is an organic acid derivative.

In an exemplary embodiment for compounds having Formula (I), $R^6$ is methyl or ethyl; $R^7$ is hydroxyl or amino; and n is 0 to 2.

Salts of compounds having Formula (I) are also suitable for certain embodiments. Representative salts of the compound of Formula (I) include the ammonium, magnesium, calcium, lithium, sodium, potassium, selenium, iron, copper, and zinc salts. In a preferred embodiment, the compound of Formula (I) is in the form of the calcium salt. Representative amides include methylamide, dimethylamide, ethylmethylamide, butylamide, dibutylamide, butylmethylamide, alkyl ester of N-acyl methionates (e.g., alkyl N-acetyl methionates. Representative esters include the methyl, ethyl, n-propyl, isopropyl, butyl esters, namely n-butyl, sec-butyl, isobutyl, and t-butyl esters, pentyl esters and hexyl esters, especially n-pentyl, isopentyl, n-hexyl and isohexyl esters.

In various exemplary embodiments, the compound of Formula (I) is 2-hydroxy-4-(methylthio)butanoic acid (HMTBA) or a salt, amide or ester thereof, such as any of those detailed above. In still more preferred embodiments, the compound of Formula (I) is HMTBA.

i. Mixtures of Acidifying Agents

The Acidifying Agent May Comprise a Mixture of Two, Three, Four, five, or six or more of the individual organic acids detailed above. The mixture of organic acids, by way of non-limiting example, may be selected from the group consisting of formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, 2-hydroxy-4-methylthiobutanoic acid, and glutaric acid.

In an exemplary embodiment, the mixture of organic acids is selected from the group consisting of 2-hydroxy-4-methylthiobutanoic acid, formic acid, butyric acid, fumaric acid, lactic acid, benzoic acid, phosphoric acid, propionic acid, sorbic acid, and citric acid. In one alternative of this embodiment, the mixture of organic acids comprises 2-hydroxy-4-methylthiobutanoic acid, butyric acid, and propionic acid. In still another alternative of this embodiment, the mixture of organic acids comprises 2-hydroxy-4-methylthiobutanoic acid, butyric acid, lactic acid, and propionic acid. In another alternative of this embodiment, the mixture of organic acids comprises 2-hydroxy-4-methylthiobutanoic acid, formic acid, and phosphoric acid. In yet another alternative of this embodiment, the mixture of organic acids comprises 2-hydroxy-4-methylthiobutanoic acid, formic acid, and propionic acid. In a further alternative of this embodiment, the mixture of organic acids comprises 2-hydroxy-4-methylthiobutanoic acid, formic acid, lactic acid, and phosphoric acid. In an additional alternative embodiment, the mixture of organic acids comprises formic acid, fumaric acid, and sorbic acid. In another alternative of this embodiment, the mixture of organic acids comprises formic acid and propionic acid. In yet another alternative of this embodiment, the mixture of organic acids comprises formic acid, fumaric acid, and lactic acid. In an exemplary alternative of this embodiment, the mixture of organic acids comprises 2-hydroxy-4-methylthiobutanoic acid, fumaric acid, and benzoic acid.

ii. Protection of Acidifying Agent

The acidifying agent or mixture of acidifying agents may be protected such that release of an intact acidifying agent occurs in the distal portion of the gastrointestinal tract. As will be appreciated by a skilled artisan, the acidifying agent may be formulated for release in the distal portion of the gastrointestinal tract by several suitable methods known in the art. In one embodiment, the acidifying agent may be encapsulated. In an exemplary embodiment, the acidifying agent may be embedded in a matrix.

One aspect of the invention provides a composition comprising an acidifying agent that is embedded in a matrix comprising a fat source. A variety of compounds or compositions are suitable for use as a matrix. In the context of the invention, the term "matrix" is used in its broadest sense and includes any of a variety of compounds or compositions to which a composition comprising an organic acid and a fatty acid may be embedded. In an exemplary embodiment, the matrix will comprise a fat source. Generally speaking, a suitable matrix is one that can be embedded with a relatively high density of a composition comprising either a mixture of organic acids or a mixture of at least one organic acid and at least one fatty acid. In the context of the invention, the term "embedded" generally means that the acidifying agents forming the composition are disposed on the surface of or within the matrix. The term "matrix-embedded" does not include encapsulated products, which are described below. Encapsulated products typically contain 100% of the acidifying disposed inside of a protective coating or barrier. In an exemplary embodiment, the matrix will comprise a fat source. The fat source may be an animal fat. Examples of animal fat include lard or butter. Alternatively, the fat source may be a vegetable fat. Examples of vegetable fats include coconut oil, palm oil, cottonseed oil, wheat germ oil, soy oil, olive oil, corn oil, sunflower oil, safflower oil, and rapeseed oil.

Alternatively, the acidifying agent may be formulated for intact release in the distal portion of the gastrointestinal tract by microencapsulation or by a dry coating process. By varying the amount and type of coating and its thickness, the timing and location of release of the acidifying agent may be controlled. The coating can and will vary depending upon a variety of factors, including, the particular acidifying agent, and the purpose to be achieved by its encapsulation. The coating material may be a biopolymer, a semi-synthetic polymer, or a mixture thereof. The microcapsule may comprise one coating layer or many coating layers, of which the layers may be of the same material or different materials. In one embodiment, the coating material may comprise a polysaccharide or a mixture of saccharides and glycoproteins extracted from a plant, fungus, or microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In another embodiment, the coating material may comprise a protein. Suitable proteins include, but are not limited to, gelatin, casein, collagen, whey proteins, soy proteins, rice protein, and corn proteins. In an alternate embodiment, the coating material may comprise a fat or oil, and in particular, a high temperature melting fat or oil. The fat or oil may be hydrogenated or partially hydrogenated, and preferably is derived from a plant. The fat or oil may comprise glycerides, free fatty acids, fatty acid esters, or a mixture thereof. In still another embodiment, the coating material may comprise an edible wax. Edible waxes may be derived from animals, insects, or plants. Non-limiting examples include beeswax, lanolin, bayberry wax, carnauba wax, and rice bran wax. The coating material may also comprise a mixture of biopolymers. As an example, the coating material may comprise a mixture of a polysaccharide and a fat.

In an exemplary embodiment, the coating may be an enteric coating. The enteric coating generally will provide for controlled release of the acidifying agent, such that intact release can be accomplished at some generally predictable location in the lower intestinal tract below the point at which intact release would occur without the enteric coating. In certain embodiments, multiple enteric coatings may be utilized. Multiple enteric coatings, in certain embodiments, may be selected to release the acidifying agent or combination of acidifying agents at various regions in the lower gastrointestinal tract and at various times. The enteric coating is typically, although not necessarily, a polymeric material that is pH sensitive. A variety of anionic polymers exhibiting a pH-dependent solubility profile may be suitably used as an enteric coating in the practice of the present invention to achieve delivery of the active to the lower gastrointestinal tract. Suitable enteric coating materials include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonia methylacrylate, ethyl acrylate, methyl methacrylate and/or ethyl methacrylate (e.g., those copolymers sold under the trade name EUDRAGIT®); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). Combinations of different coating materials may also be used to coat a single capsule.

As will be appreciated by a skilled artisan, the encapsulation or coating method can and will vary depending upon the acidifying agents used to form composition and coating, and the desired physical characteristics of the microcapsules themselves. Additionally, more than one encapsulation methods may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art.

(b) Immune Stimulating Agent

The premix compositions of the invention also comprise at least one immune stimulating agent. As used herein, an "immune stimulating agent" is an agent that can stimulate immune function of the recipient by a variety of mechanisms, such as by improving the recipient's physiological defenses.

Suitable immune stimulating agents include minerals, vitamins, probiotics, and prebiotics. Exemplary vitamins and minerals include those that enhance immune function such as Vitamin E, Vitamin D, zinc, copper, and selenium.

Probiotics and prebiotics include yeast and bacteria that help establish an immune protective gut microflora as well as small oligosaccharides. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent is β-glucans and/or mannanoligosaccharides. Sources for yeast cell wall derived components include *Saccharomyces bisporus*, *Saccharomyces boulardii*, *Saccharomyces cerevisiae*, *Saccharomyces capsularis*, *Saccharomyces delbrueckii*, *Saccharomyces fermentati*, *Saccharomyces lugwigii*, *Saccharomyces microellipsoides*, *Saccharomyces pastorianus*, *Saccharomyces rosei*, *Candida albicans*, *Candida cloaceae*, *Candida tropicalis*, *Candida utilis*, *Geotrichum candidum*, *Hansenula americana*, *Hansenula anomala*, and *Hansenula wingei*.

Probiotics and prebiotics also include bacteria cell wall derived agents such as peptidoglycan and other components derived from gram-positive bacteria with a high content of peptidoglycan. Exemplary gram-positive bacteria include lactobacillus, bactobacillus and bifidobacteria.

(c) Antioxidant

The pre-mix compositions also include at least one antioxidant. In some embodiments, the antioxidant may be a compound that interrupts the free-radical chain of oxidative reactions by protonating free radicals, thereby inactivating them. Alternatively, the antioxidant may be a compound that scavenges the reactive oxygen species. In other embodiments, the antioxidant may be a compound that chelates the metal catalysts. In still other embodiments, the antioxidant may be a synthetic compound, a semi-synthetic compound, or a natural (or naturally-derived) compound.

In one embodiment, the antioxidant is a quinoline compound. Typically, the quinoline compound will be a substituted 1,2-dihydroquinoline. Substituted 1,2-dihydroquinoline compounds suitable for use in the invention generally correspond to formula (II):

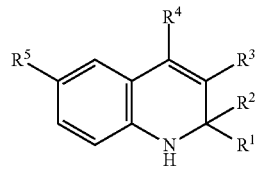

(II)

wherein:

$R^1$, $R^2$, $R^3$ and $R^4$ are independently selected from the group consisting of hydrogen and an alkyl group having from 1 to about 6 carbons; and $R^5$ is an alkoxy group having from 1 to about 12 carbons.

In another embodiment, the substituted 1,2-dihydroquinoline will have formula (II) wherein:

$R^1$, $R^2$, $R^3$ and $R^4$ are independently selected from the group consisting of hydrogen and an alkyl group having from 1 to about 4 carbons; and $R^5$ is an alkoxy group having from 1 to about 4 carbons.

In an exemplary embodiment, the substituted 1,2-dihydroquinoline will be 6-ethoxy-1,2-dihydro-2,2,4-trimethylquinoline having the formula:

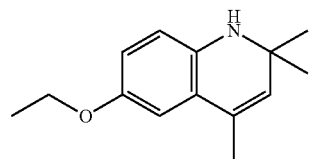 [SMILES: CCOc1ccc2c(c1)C(C)=CC(C)(C)N2]

The compound, 6-ethoxy-1,2-dihydro-2,2,4-trimethylquinoline, is commonly known as ethoxyquin.

Additional suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (paba), butylated hydroxyanisole (bha), butylated hydroxytoluene (bht), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, n,n'-diphenyl-p-phenylenediamine (dppd), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (edta), eucalyptus extract, eugenol, ferulic acid, flavonoids (e.g., catechin, epicatechin, epicatechin gallate, epigallocatechin (egc), epigallocatechin gallate (egcg), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, lactic acid and its salts, lecithin, lecithin citrate; r-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (ndga), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rice bran extract, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., ionox 100), 2,4-(tris-3',5'-bi-tert-butyl-4'-hydroxybenzyl)-mesitylene (i.e., ionox 330), 2,4,5-trihydroxybutyrophenone, ubiquinone, tertiary butyl hydroquinone (tbhq), thiodipropionic acid, trihydroxy butyrophenone, tryptamine, tyramine, uric acid, vitamin k and derivates, vitamin q10, wheat germ oil, zeaxanthin, or combinations thereof.

Exemplary antioxidants include synthetic phenolic compounds, such as TBHQ, BHA, or BHT; gallic acid derivatives, such as n-propyl gallate; Vitamin C derivatives, such as ascorbyl palmitate; lecithin; and Vitamin E compounds, such as, alpha-tocopherol.

In additional embodiments, the antioxidant may comprise a mixture of two, three, four, or five or more of any of the antioxidants detailed herein or otherwise known in the art. In one exemplary embodiment, the antioxidant combination is 6-ethoxy-1,2-dihydro-2,2,4-trimethylquinoline and any of the natural antioxidants detailed herein. In a further exemplary embodiment, the antioxidant combination is 6-ethoxy-1,2-dihydro-2,2,4-trimethylquinoline and any of the synthetic antioxidants detailed herein. In yet another embodiment, the antioxidant combination is 6-ethoxy-1,2-dihydro-2,2,4-trimethylquinoline and any of the semi-synthetic antioxidants detailed herein. In one alternative embodiment, the antioxidant combination comprises 6-ethoxy-1,2-dihydro-2,2,4-trimethylquinoline and BHA. In still another exemplary embodiment, the antioxidant combination is 6-ethoxy-1,2-dihydro-2,2,4-trimethylquinoline and BHT. In a further exemplary embodiment, the antioxidant combination is 6-ethoxy-1,2-dihydro-2,2,4-trimethylquinoline and TBHQ.

(d) Tissue Regeneration Agent

The pre-mix compositions of the invention optionally may include one or more tissue regeneration agents.

Exemplary tissue regeneration agents generally include esters of polyols. Suitable polyols typically have at least one accessible hydroxyl group. In this context, the term "accessible" means the hydroxyl group of the polyol is capable of forming an ester bond with a compound containing a carboxyl group. More typically, the polyol may have three or more hydroxyl groups. A suitable polyol having three hydroxyl groups is glycerol. In other embodiments, the polyol may be a sugar alcohol having four to six hydroxyl groups. Examples of suitable sugar alcohols include erythritol, xylitol, sorbitol, maltitol and mannitol. In an alternative embodiment, the polyol may be an oligosaccharide or polysaccharide having at least one accessible hydroxyl group. Inulin is an example of a suitable oligosaccharide.

In an exemplary embodiment, the polyol ester is a compound comprising Formula (III):

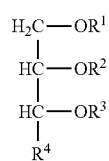

(III)

wherein:
$R^1$, $R^2$, and $R^3$ are independently selected from the group consisting of hydrogen, an amino acid, and a carboxylic acid or a substituted carboxylic acid having from two to twenty-two carbon atoms;
$R^4$ is hydrogen or $(CH_2OR^5)_m$;
m is an integer from 1 to 3; and
$R^5$ is independently selected from the group consisting of hydrogen, an amino acid, and a carboxylic acid or a substituted carboxylic acid having from two to twenty-two carbon atoms.

For each of the foregoing embodiments for polyol esters comprising Formula (III), $R^4$ may be hydrogen. Alternatively, $R^4$ may be $(CH_2OR^5)_m$. In certain embodiments, m is one. In other embodiments, m is two. In additional embodiments, m is three.

In yet another alternative exemplary embodiment, the polyol ester is a glycerol ester comprising Formula (IV):

wherein:
$R^1$, $R^2$, and $R^3$ are independently selected from the group consisting of hydrogen, a carboxylic acid or substituted carboxylic acid having from two to twenty-two carbon atoms, and an amino acid.

For any of the above-embodiments, the carboxylic acid compound may be a monocarboxylic acid having a straight chain or it may be branched; it may be saturated or unsaturated. In one embodiment, the carboxylic acid may contain from about two to about twenty-five carbon atoms. In another embodiment, the carboxylic acid may have from about three to about twenty-two carbon atoms. In a further embodiment, the carboxylic acid may contain from about three to about twelve carbon atoms. In yet another embodiment, the carboxylic acid may contain from about eight to about twelve carbon atoms. In still another embodiment, the carboxylic acid may contain from about two to about six carbon atoms. By way of non limiting example, the carboxylic acid may be a saturated aliphatic compound selected from the group consisting of propionic acid, butanoic acid, pentaenoic acid, caproic or hexanoic acid, heptanoic acid, caprylic or octanoic acid, nonanoic acid, capric or decanoic acid, undecanoic acid, lauric or dodecanoic acid, tridecanoic acid, myristic or tetradecanoic acid, pentadecanoic acid, palmitic or hexadecanoic acid, margaric or heptadecanoic acid, stearic or octadecanoic acid, nonadecanoic acid, arachidic or eicosanoic acid, and behenic or docosanoic acid. Alternatively, the carboxylic acid may be an unsaturated aliphatic compound selected from the group consisting of sorbic acid, a hexanoic acid with two double bonds (6:2), myristoleic acid (i.e., a $C_{14}$ acid with one double bond (14:1)), palmitoleic acid (16:1), oleic acid (18:1), linoleic acid (18:2), linolenic (18:3), gadoleic acid (20:1), and arachidonic acid (20:4).

Alternatively, the carboxylic acid compound may be a substituted carboxylic acid. A substituted carboxylic acid generally has the same features as those detailed above for carboxylic acids, but the hydrocarbyl chain has been modified such that it is branched, is part of a ring structure, or contains some other substitution. In one embodiment, the substituted carboxylic acid may contain one or more additional carboxyl groups. Saturated dicarboxylic acids include malonic acid, succinic acid, glutaric acid, and adipic acid, and unsaturated dicarboxylic acids include maleic acid and fumaric acid. In another embodiment, the substituted carboxylic acid may contain one or more hydroxyl groups. A substituted carboxylic acid with a hydroxyl group on the alpha carbon, i.e., the carbon adjacent to the carboxyl carbon, is generally called a α-hydroxy carboxylic acid. Examples of suitable α-hydroxy carboxylic acids include glycolic acid, lactic acid, malic acid, and tartaric acid. In an alternate embodiment, the substituted carboxylic acid may contain one or more carbonyl groups. In yet another embodiment, the substituted carboxylic acid may contain an amino group on the alpha carbon, i.e., is an α-amino acid. In one embodiment, the α-amino acid may be one of the twenty standard amino acids or derivatives thereof. In another embodiment, the α-amino acid may be an essential α-amino acid selected from the group consisting of arginine, histidine, isoleucine, leucine, lysine, methionine, phenylalanine, threonine, tryptophan, and valine.

In yet another embodiment, the substituted carboxylic acid may be a compound having Formula (I):

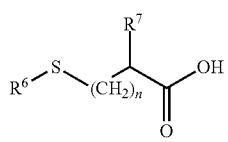

(I)

wherein:
n is an integer from 0 to 2;
$R^6$ is an alkyl group having from one to four carbon atoms;
$R^7$ is selected from the group consisting of hydroxyl, amino, and —$OCOR^8$ or —$NHCOR^8$; and
$R^8$ is an organic acid derivative.

In an exemplary embodiment for compounds having Formula (I), $R^6$ is methyl or ethyl; $R^7$ is hydroxyl or amino; and n is 0 to 2.

In one exemplary embodiment, the tissue regeneration agent is a mono, di, or tri-ester of glycerol. Exemplary esters of glycerol include those having propanoic acid, butanoic acid, pentaenoic acid, caproic or hexanoic acid, heptanoic acid, caprylic or octanoic acid, nonanoic acid, capric or decanoic acid, and 2-hydroxy-4-methylthiobutanoic acid.

(e) Combination of Ingredients

The choice of individual ingredients forming the pre-mix composition of the invention can and will vary without departing from the spirit of the invention. As such, the pre-mix composition may comprise any combination of acidifying agents, immune stimulating agents, antioxidants, and optionally tissue regeneration agents as detailed herein (i.e., in (I)(a) to (d) above) or otherwise known in the art.

In one exemplary embodiment, the pre-mix composition comprises:
at least one acidifying agent selected from the group consisting of 2-hydroxy-4-methylthiobutanoic acid, formic acid, butyric acid, fumaric acid, lactic acid, benzoic acid, phosphoric acid, propionic acid, sorbic acid, and citric acid;
at least one immune stimulating agent selected from the group consisting of a yeast derived product, a bacterial derived product, and combinations thereof; and
at least one antioxidant selected from the group consisting of 6-ethoxy-1,2-dihydro-2,2,4-trimethylquinoline, tertiary butyl hydroquinone, butylated hydroxyanisole, butylated hydroxytoluene, gallic acid or derivative of gallic acid, lecithin, ascorbic acid, and tocopherol.

In yet another exemplary embodiment, the pre-mix composition further comprise a tissue regeneration agent that is an ester of a compound comprising Formula (IV):

(IV)

wherein:
$R^1$, $R^2$, and $R^3$ are independently selected from the group consisting of hydrogen, a carboxylic acid or substituted carboxylic acid having from three to twelve carbon atoms, and an amino acid.

In an additional exemplary embodiment, the pre-mix composition comprises an acidifying agent comprising 2-hydroxy-4-methylthiobutanoic acid, fumaric acid, and benzoic acid; an immune stimulating agent comprising mannan oligosaccharide and beta-glucans; and an antioxidant comprising 6-ethoxy-1,2-dihydro-2,2,4-trimethylquinoline. In yet another alternative of this embodiment, the pre-mix composition further comprises a tissue regeneration agent that is a glycerol ester of butanoic acid. In still another alternative of this embodiment, the antioxidant may comprise a mixture of 6-ethoxy-1,2-dihydro-2,2,4-trimethylquinoline and TBHQ. Other exemplary non-limiting examples of pre-mix compositions of the invention are described in the examples.

As will be appreciated by a skilled artisan the amount of each ingredient forming the pre-mix composition also can and will vary. The acidifying agent, for example, may comprise at least 30%, at least 40%, at least 50%, at least 60%, at least 70%, or greater than at least 80% by weight of the pre-mix composition. The antioxidant may comprise at least 1%, at least 5%, at least 10%, at least 15%, or greater than about 20% by weight of the pre-mix composition. The immune stimulating agent may comprise at least 1%, 2%, 3%, 4%, 5%, 6%, 7%, 8%, 9%, 10%, 11%, 12%, 13%, 14%, or greater than about 15% by weight of the pre-mix composition. The tissue regenerating agent may comprise at least 1%, at least 5%, at least 10%, at least 15%, or greater than about 20% by weight of the pre-mix composition.

(II) Piglet Feed Rations

The pre-mix compositions of the invention may be utilized to replace fermentable carbohydrates, such as lactose or whey, commonly used in piglet feed rations. As utilized herein, "piglet feed rations" generally refer to feed rations provided to piglets from the time of weaning to about the grower/finisher stage. In this context, the term generally refers to the feed ration provided to pigs that are from about three weeks of age to about seven weeks of age. Generally speaking, piglet feed rations comprise two distinct phases: Phase I includes feed rations fed to piglets from about one day to about ten days post weaning, and Phase II includes feed rations fed to piglets from about ten day to about twenty-one days post weaning.

Common ingredients in piglet feed rations typically comprise grains (e.g., corn, barley, grain sorghum, oats, soybeans, wheat, etc.), crude proteins (e.g., fish meal, gluten meal, meat meal, soybean meal, tankage, which is the residue that remains after rendering fat in a slaughterhouse, etc.), crude fat (e.g., fish oils, vegetable oils, animal fats, yellow grease, etc.), supplemental amino acids (e.g., lysine, methionine or methionine analogs, etc), vitamins, minerals, mycotoxin inhibitors, antifungal agents, and pharma/nutriceuticals. Exemplary Phase I and Phase II feed rations are provided in the Examples (e.g., see Tables 1, 8, and 18 for Phase I feed rations, and Tables 4, 10, and 20 for Phase II feed rations). Phase I formulations generally comprise from about 15% to about 30% by weight lactose. Phase II formulations generally comprise from about 4% to about 12% by weight lactose.

It is envisioned, as stated above, that the pre-mix composition of the invention may be substituted for all or a portion of the fermentable carbohydrate commonly included in Phase I and/or Phase II piglet feed rations. As such, the pre-mix may replace from about 1% to about 100% of the fermentable carbohydrate commonly included in piglet feed rations. In other embodiments, the pre-mix composition may replace from about 5%, 10%, 15%, 20%, 25%, 30%, 35%, 40%, 45%, 50%, 55%, 60%, 65%, 70%, 75%, 80%, 90%, 95%, or 100% of the fermentable carbohydrate commonly included in piglet feed rations. In an alternative embodiment, the pre-mix composition may be used to replace greater than about 50% of the fermentable carbohydrate commonly included in a Phase I piglet feed ration, and greater than about 75% of the fermentable carbohydrate commonly included in a Phase II piglet feed ration. By way of non-limiting example, when the fermentable carbohydrate is lactose, the pre-mix composition may be used to replace about 50% of the lactose in a Phase I diet, such that the diet includes from about 7% to about 15% by weight lactose instead of from about 15% to about 30% by weight lactose. By way of further non-limiting example, when the fermentable carbohydrate is lactose, the pre-mix composition may be used to replace about 75% of the lactose in a Phase II diet, such that the diet includes from about 1% to about 3% by weight lactose instead of from about 4% to about 12% by weight lactose. Stated another way, for a Phase I diet, the feed ration may comprise from about 0.5% to about 1% by weight of the pre-mix composition of the invention. For a Phase II diet, the feed ration may comprise from about 0.2% to about 1% by weight of the pre-mix composition of the invention.

(III) Milk Replacers

The pre-mix compositions of the invention may be utilized to replace all or a portion of fermentable carbohydrates commonly used in dry powdered milk replacers, such as lactose or whey. For example, the pre-mix composition may be utilized in milk replacers to replace from about 5%, 10%, 15%, 20%, 25%, 30%, 35%, 40%, 45%, 50%, 60%, 70%, 80%, 90%, 95%, or 100% of fermentable carbohydrates in milk replacers.

(a) Ingredients

Typically, the milk replacers of the invention will include an amount of the pre-mix composition along with other ingredients necessary to meet the dietary requirements for a neonatal mammalian animal. As will be appreciated by a skilled artisan, these ingredients can and will vary depending on the mammalian species. Conventional milk replacers, for example, generally comprise crude protein from milk sources, fats, fiber, vitamins, vitamins (e.g., vitamin A, vitamin B group, vitamins C, D and E, etc.), and inorganic substances (e.g., calcium, calcium phosphate, calcium carbonate, phosphorus, sodium, selenium, etc.). Illustrative non-limiting examples of milk replacer compositions for several mammalian species are shown below.

|  | Piglet | Calf | Foal | Kid | Lamb | Ungulate (deer/elk) |
|---|---|---|---|---|---|---|
| Protein (min. %) | 24 | 20-26 | 20 | 22 | 23 | 30 |
| Protein from Milk Source (min. %) | 24 | 20-26 | 20 | 22 | 23 | 30 |
| Fat (min. %) | 14 | 16 | 15 | 20 | 30 | 35 |
| Fiber (max. %) | 0.10 | 0.15-0.25 | 0.15 | 0.25 | 0.25 | 0.25 |
| Calcium (%) | 1.00 | 0.9-1.00 | 0.90 | 0.80 | 0.80 | 1.00 |
| Phosphorus (%) | 0.85 | 0.80 | 0.80 | 0.70 | 0.60 | 0.80 |
| Sodium (%) | 0.65 | 0.50-0.80 | 0.80 | 0.50 | 0.50 | 0.50 |
| Selenium (mg/kg) | 0.30 | 0.30 | 0.30 | 0.30 | 0.30 | 0.30 |
| Vitamin A (min. IU/kg) | 20000 | 56000-65000 | 40000 | 40000 | 55000 | 56000 |
| Vitamin D3 (min. IU/kg) | 1500 | 16000-17000 | 5000 | 3000 | 10000 | 10000 |
| Vitamin E (min. IU/kg) | 300 | 350 | 300 | 300 | 300 | 300 |
| Zinc (mg/kg) | 270 | — | — | — | — | — |
| Copper (mg/kg) | 90 | — | — | — | — | — |

The pre-mix composition, as detailed above, may be utilized in the milk replacer compositions of the invention to replace from about 5%, 10%, 15%, 20%, 25%, 30%, 35%, 40%, 45%, 50%, 60%, 70%, 80%, 90%, 95%, or 100% of the fermentable carbohydrates.

In addition, the milk replacer compositions may include a variety of different components such as one or more proteinaceous ingredient(s), a fat base, a liquid fat-based blend, one or more dietary additives, and one or more emulsifying agents. Suitable examples of such ingredients are detailed below.

The proteinaceous ingredient(s) may be derived from animal sources, plant sources, or any combination of animal sources and plant sources. Some examples of suitable animal-derived proteinaceous ingredient(s) that may be incorporated include dairy materials, such as whey, whey protein, whey protein concentrate, whey permeate, de-lactosed whey, casein, and dried milk protein; fishmeal, such as fish protein meal; animal fluids, such as blood, components of blood, and subfractions of blood; microbial biomass, such as single cell protein; and any of these in any combination. Examples of suitable plant-derived proteinaceous ingredient(s) include protein flours and protein-enriched flours derived from grains, such as soybeans, rapeseed, sunflower seeds, wheat, and peanuts; protein flours derived from vegetables, such as potatoes; and any of these in any combination.

The fat source serves as the primary energy source in the milk replacer composition. Non-exhaustive examples of suitable components of the fat source include animal fat, such as lard, beef tallow, butter, chicken fat, milk fat, sheep fat, and deer fat; vegetable fat, such as soybean oil, safflower oil, oil of evening primrose, marine oil, linseed oil, rapeseed oil, corn oil, rice oil, coconut oil, and castor oil; fatty acids, such as lauric, myristic, palmitic, stearic, arachidonic, palmitoleic, oleic, linoleic, linolenic, and alphalinolenic acid; sugars, such as glucose, fructose, sucrose, lactose, galactose; corn syrup; starch, such as rice starch, wheat starch, corn starch, tapioca, and potato starch; modified starch, such as acetylated starch, and hydroxy propyl starch; water; proteinaceous ingredient(s), such as any of the proteinaceous ingredients detailed herein, and any of these in any combination.

Some non-exhaustive examples of other dietary additives that may be included in the milk replacer composition include organic acids, such as malic, acetic, citric, propionic, and lactic acids that are added to improve the keeping qualities of the rehydrated milk; antibiotics, such as neomycin and terramycin; soluble fiber from sources such as psyllium, oats, dried brewers' grains, sugar beet pulp, and yeast; vitamins, such as, A, D, E, K, B-complex vitamins, C and B-carotene; minerals such as calcium, phosphorous, magnesium, sodium, potassium, chloride, selenium, copper, iron, manganese, cobalt, zinc, iodine, and sulphur; silicate to help ensure a free flowing powder; immune stimulating agents to help improve the resistance to disease; and any combination of any of these dietary additives.

(b) Agglomeration Process

Generally speaking, the milk replacer compositions of the invention are provided as dry powders, which are reconstituted with water to form liquid solutions. As such, the pre-mix compositions are typically manufactured utilizing an agglomeration process in order to provide an ingredient that is water-soluble.

Suitable agglomeration processes typically provide milk compositions that instantizes, or agglomerates, dry blended powder to create a product that mixes easily, wets correctly, and stays in solution once mixed. This process begins with a hydrator where moisture is added to dry powder ingredients. As these particles fall down through the hydrator they stick to each other, forming snowflake-like agglomerates. The wet particles are held for a period, providing time for the water to further soak into the powder particles. A dryer then removes the added moisture. Once dried, the crystalline, agglomerated particles create capillary action when mixed with water, allowing easy mixing of the product.

For example, to produce a milk replacer, a powdered nutritional composition is introduced into a mixer to agglomerate the powdered nutritional composition and thereby increase its particle size. One or more agglomerating agent(s) and one or more emulsifying agent(s) may also be introduced into the mixer along with the powdered nutritional composition to facilitate the agglomeration process. Alternatively, an emulsifying agent may be included as part of the powdered nutritional composition instead of, or in addition to, the emulsifying agent(s) that may be introduced directly into the mixer.

The mixer, with the aid of the optional agglomerating agent(s) and the optional emulsifying agent(s), transforms the powdered nutritional composition into an agglomerated intermediate. The agglomerated intermediate is transferred from the mixer to a dryer to reduce the moisture content of, and optionally cool, the agglomerated intermediate, while preferably maintaining the particle shape and size distribution of the agglomerated intermediate. A dried agglomerated intermediate is then transferred from the dryer to a classifier to sort the dried agglomerated intermediate according to size and yield a classified milk replacer composition. The classified milk replacer composition is then ready for packaging.

Suitable agglomerating agent(s) include atomized water, atomized steam, any combination of atomized water and atomized steam, and/or a sugar, solution, such as corn syrup and/or maltodextrins blended with water. Suitable emulsifying agent(s) include lard; lecithin, such as fluid soy lecithin; polyethylene glycol; propylene glycol; ethoxylated monoglycerides of edible $C_{12}$-$C_{24}$ fatty acids; ethoxylated diglycerides of edible $C_{12}$-$C_{24}$ fatty acids; distilled monoglycerides of edible $C_{12}$-$C_{24}$ fatty acids; distilled diglycerides of edible $C_{12}$-$C_{24}$ fatty acids; and any combination of any of these.

DEFINITIONS

The term "acyl" denotes a radical having the general formula RCO—, provided after the removal of a hydroxyl group from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, and trifluoroacetyl. Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "carboxylic acid" used herein refers to organic acids comprising hydrocarbon groups that contain a carboxyl group (COON). The hydrocarbon moiety consists exclusively of the elements carbon and hydrogen. Carboxylic acids may have straight chains (aliphatic) of hydrocarbyl groups, or they may be aromatic carboxylic acids, as well as some alicyclic carboxylic acids (i.e., both aliphatic and cyclic). Straight chain aliphatic carboxylic acids preferably have 3 to 24 carbons (including the terminal carboxyl carbon). The hydrocarbon chain of an aliphatic carboxylic acid may be saturated (i.e., the carbon atoms have all the hydrogen atoms they can hold) and contain no double bonds between the carbons. Alternatively, the hydrocarbon chain may be unsaturated and contain one or more double bonds between the some of the carbons. Unsaturated carboxylic acids may assume cis or trans configurations, which refer to the orientation of the hydrogen atoms with respect to the double bond. C is means "on the same side" and trans means "across" or "on the other side".

An "essential amino acid" is an amino acid that cannot be synthesized by an organism and must be supplied as part of its diet. It is generally recognized that ten amino acids are essential for humans and animals. The essential amino acids are arginine, histidine, isoleucine, leucine, lysine, methionine, phenylalanine, threonine, tryptophan, and valine.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "inulin" refers to a type of plant oligosaccharide mainly comprising fructose units, linked by β-(2,1) glycosidic bonds, and typically having a terminal glucose unit. The simplest inulin has two fructose units and one glucose unit.

The term "organic acid derivative" refers to a derivative of any suitable organic acid resulting from removal of the carboxyl function from the acid. Preferably, the organic acid has from one to eight carbon atoms. Suitable organic acid derivatives include, but are not limited to, derivatives of formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, and glutaric acid.

The term "polyol" is used in its broadest sense to encompass a compound having at least one accessible hydroxyl group. Generally, the compound may have three or more hydroxyl groups. As used herein, those having three hydroxyl groups are glycerols; those having four to six hydroxyl groups are called sugar alcohols (e.g., erythritol, xylitol, sorbitol, mannitol); and those with many more hydroxyl groups include oligosaccharides and polysaccharides (e.g., inulin).

The term "substituted carboxylic acid" used herein refers to substitutions within the hydrocarbyl chain of a straight chain aliphatic carboxylic acid. Hydrocarbyl moieties may be substituted with at least one atom, including the substitution of a carbon atom with a heteroatom such as nitrogen, oxygen, silicon, phosphorous, boron, sulfur, or a halogen atom. Substitutions may also include hydrocarbyl moieties, such as alkyl, alkenyl, alkynyl, and aryl moieties, with these moieties having one to 20 carbon atoms. Other substituted moieties include hydrocarbyloxy, such as acyloxy, alkoxy, alkenoxy, alkynoxy, aryloxy, hydroxy, protected hydroxy, keto, acyl, acyloxy, nitro, amino, amido, cyano, thiol, ketals, acetals, heterocyclo, esters and ethers. Dicarboxylic acids contain an additional carboxyl group at the other end of the molecule. α-Hydroxy acids are another type of substituted carboxylic acid; α-hydroxy acids generally have a hydroxyl group on the alpha carbon atom (i.e., the carbon adjacent to the terminal carbonyl carbon). α-Amino acids, which have an amino group on the alpha carbon, are also substituted carboxylic acids.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the invention.

Example 1

Effect of Lactose Level and an Acidifying Agent in Nursery Pigs

The following study was designed to determine whether a feed supplement comprising an acidifying agent could counteract the negative effects of lower levels of lactose in nursery pigs. A two-phase feeding program, with and without an acidifying agent comprising 2-hydroxy-4-methylthiobutanoic acid, fumaric acid, and benzoic acid (i.e., as provided by ACTIVATE® DA, Novus Intl), was implemented with industry norms for energy, digestible amino acids, vitamins, and minerals. The two-phase feeding program introduced ingredients in a progressive way to gently enhance maturation of the gastrointestinal system, while at the same time supplying special ingredients that should encourage maximal growth performance. The pigs were fed a Phase I diet from weaning to 10 days post weaning, and a Phase II diet from days 11 to 21 post weaning. The levels of lactose were varied in each diet phase and each level of lactose was examined with and without the acidifying agent.

a. Animals and Measurements

A total of approximately 840 commercial breed nursery pigs (TR-4×C22 PIC lines, PIC Intl., Franklin, Ky.) were blocked by weight and sex, and then placed into a pen containing about 20-22 pigs per pen. There were a total of 42 pens that were used for 7 replications/treatment with approximately equal numbers of pens per sex/treatment. Treatments were randomly assigned to pens within a room prior to treatment initiation. Each pen was accounted as an experimental unit. The animals were cared for according to standard site practices, which include daily observations, temperature monitoring, feeder observations, and waterer observations.

Diets were balanced to meet 60 TID Met & Cys:Lys. The ideal amino acid ratio of Thr, Tryp, Ile, and Val to Lys was maintained at a minimum of 65%, 16%, 55%, and 65%, respectively, based on the TID ideal amino acid profile for swine. Diets that included the acidifying agent used MHA (DL-methionine hydroxyl analog) to balance for the methionine source, while diets without the acidifying agent used DL-Met as a methionine source. All diets were balanced to have equivalent methionine activity and properly mixed according to the diet formulations presented in Table 1 and Table 2 for Phase I, and Table 4 and Table 5 for Phase II. Calculated analyses of the diets are presented in Tables 3 and 6 for Phase I and II, respectively.

The treatment arrangements were a 3×2 factorial arrangement with three levels of lactose with and without the acidifying agent (i.e., ACTIVATE® DA at a 0.5%). Diets were formulated to provide 5%, 10%, or 20% lactose equivalent during Phase I (0 to 10 days post weaning) and 2.5%, 5%, or 10% lactose equivalent during Phase II (11 to 21 days post weaning). The lactose equivalent was provided by DAIRY-LAC-80® (80% lactose content; International Ingredient Corporation, St. Louis, Mo.). Fishmeal and SDPP were held constant across the diets, and corn and CWG were allowed to float to provide similar energy levels. All diets were supplemented with the enteric antibiotic carbodox (i.e., MECA-DOX®, Phibro Animal Health, Ridgefield Park, N.J.).

TABLE 1

Phase I Diet Composition.

| Ingredient (%) | 5% Lactose | | 10% Lactose | | 20% Lactose | |
|---|---|---|---|---|---|---|
| | 0 DA | 0.5% DA | 0 DA | 0.5% DA | 0 DA | 0.5% DA |
| Corn | 55.37 | 55.03 | 49.61 | 49.18 | 38.11 | 37.67 |
| SBM (soybean meal) | 25 | 25 | 25 | 25 | 25 | 25 |
| DAIRYLAC-80 | 6.25 | 6.25 | 12.5 | 12.5 | 25 | 25 |
| ACTIVATE DA | 0 | 0.5 | 0 | 0.5 | 0 | 0.5 |
| Fishmeal | 4 | 4 | 4 | 4 | 4 | 4 |
| SDPP (spray dried pig plasma | 3 | 3 | 3 | 3 | 3 | 3 |
| CWG (choice white grease) | 2 | 2 | 1.64 | 1.73 | 0.91 | 1.02 |
| Dical (calcium source) | 1.02 | 1.02 | 0.82 | 0.82 | 0.42 | 0.42 |
| Lime | 0.62 | 0.59 | 0.66 | 0.63 | 0.74 | 0.69 |
| MECADOX | 1 | 1 | 1 | 1 | 1 | 1 |
| Lys-HCl | 0.34 | 0.34 | 0.35 | 0.35 | 0.35 | 0.35 |
| Thr | 0.18 | 0.18 | 0.19 | 0.19 | 0.2 | 0.2 |
| MHA | 0 | 0.08 | 0 | 0.1 | 0 | 0.13 |
| DL-Met | 0.22 | 0 | 0.23 | 0 | 0.26 | 0 |
| Salt | 0.3 | 0.3 | 0.3 | 0.3 | 0.3 | 0.3 |
| CuSO$_4$ | 0.05 | 0.05 | 0.05 | 0.05 | 0.05 | 0.05 |
| ZnO | 0.25 | 0.25 | 0.25 | 0.25 | 0.25 | 0.25 |
| Vitamin | 0.25 | 0.25 | 0.25 | 0.25 | 0.25 | 0.25 |
| Mineral | 0.15 | 0.15 | 0.15 | 0.15 | 0.15 | 0.15 |
| | 100 | 100 | 100 | 100 | 100 | 100 |

TABLE 2

Phase I Diet Formulations.

| Ingredient (lb/ton) | 5% Lactose | | 10% Lactose | | 20% Lactose | |
|---|---|---|---|---|---|---|
| | 0 DA | 0.5% DA | 0 DA | 0.5% DA | 0 DA | 0.5% DA |
| Corn | 1107.04 | 1100.6 | 992.2 | 983.7 | 766.2 | 757.4 |
| SBM | 500 | 500 | 500 | 500 | 500 | 500 |
| DAIRYLAC-80 | 125 | 125 | 250 | 250 | 500 | 500 |
| ACTIVATE DA | 0 | 10 | 0 | 10 | 0 | 10 |
| Fishmeal | 80 | 80 | 80 | 80 | 80 | 80 |
| SDPP | 60 | 60 | 60 | 60 | 60 | 60 |
| CWG | 40 | 40 | 32.8 | 34.6 | 18.24 | 20.44 |
| Dical | 20.4 | 20.48 | 16.47 | 16.48 | 8.44 | 8.46 |
| Lime | 12.4 | 11.88 | 13.19 | 12.53 | 14.72 | 13.84 |
| MECADOX | 20 | 20 | 20 | 20 | 20 | 20 |
| Lys | 6.84 | 6.84 | 6.91 | 6.94 | 7.08 | 7.1 |
| Thr | 3.6 | 3.6 | 3.76 | 3.78 | 4.07 | 4.09 |
| MHA | 0 | 1.63 | 0 | 1.97 | 0 | 2.64 |
| DL-Met | 4.4 | 0 | 4.68 | 0 | 5.24 | 0 |
| Salt | 6 | 6 | 6 | 6 | 2 | 2 |

TABLE 2-continued

Phase I Diet Formulations.

| Ingredient | 5% Lactose | | 10% Lactose | | 20% Lactose | |
|---|---|---|---|---|---|---|
| (lb/ton) | 0 DA | 0.5% DA | 0 DA | 0.5% DA | 0 DA | 0.5% DA |
| CuSO$_4$ | 1 | 1 | 1 | 1 | 1 | 1 |
| ZnO | 5 | 5 | 5 | 5 | 5 | 5 |
| Vitamin | 5 | 5 | 5 | 5 | 5 | 5 |
| Mineral | 3 | 3 | 3 | 3 | 3 | 3 |
|  | 2000 | 2000 | 2000 | 2000 | 2000 | 2000 |

TABLE 3

Phase I Diet Calculated Analyses.

|  | 5% Lactose | | 10% Lactose | | 20% Lactose | |
|---|---|---|---|---|---|---|
|  | 0 DA | 0.5% DA | 0 DA | 0.5% DA | 0 DA | 0.5% DA |
| ME, kcal/kg | 3397 | 3400 | 3397 | 3400 | 3400 | 3400 |
| CP, % | 22 | 22.1 | 22 | 21.9 | 21.5 | 21.6 |
| Ca, % | 0.8 | 0.8 | 0.8 | 0.8 | 0.8 | 0.8 |
| P, % AV | 0.45 | 0.45 | 0.46 | 0.45 | 0.45 | 0.45 |
| Lys, Tot | 1.57 | 1.57 | 1.57 | 1.57 | 1.57 | 1.57 |
| Lys, TID | 1.43 | 1.43 | 1.43 | 1.43 | 1.43 | 1.43 |
| TID TSAA/Lys | 60 | 60 | 60 | 60 | 60 | 60 |
| TID Thr/Lys | 65 | 65 | 65 | 65 | 65 | 65 |
| TID Trp/Lys | 16.7 | 16.7 | 16.7 | 16.7 | 16.7 | 16.7 |
| TID Val/lys | 65.6 | 65.6 | 71.9 | 71.7 | 70.3 | 70 |
| TID Ile/Lys | 55 | 55 | 55 | 55 | 54 | 54 |

TABLE 4

Phase II Diet Composition.

| Ingredient | 2.5% Lactose | | 5% Lactose | | 10% Lactose | |
|---|---|---|---|---|---|---|
| (%) | 0 DA | 0.5% DA | 0 DA | 0.5% DA | 0 DA | 0.5% DA |
| Corn | 56.29 | 55.89 | 53.37 | 52.97 | 47.54 | 47.14 |
| SBM | 30 | 30 | 30 | 30 | 30 | 30 |
| DAIRYLAC-80 | 3.13 | 3.13 | 6.25 | 6.25 | 12.5 | 12.5 |
| ACTIVATE DA | 0 | 0.5 | 0 | 0.5 | 0 | 0.5 |
| Fishmeal | 4 | 4 | 4 | 4 | 4 | 4 |
| SDPP | 0 | 0 | 0 | 0 | 0 | 0 |
| CWG | 2.38 | 2.43 | 2.23 | 2.29 | 1.94 | 2.01 |
| Dical | 1.34 | 1.34 | 1.24 | 1.24 | 1.04 | 1.04 |
| Lime | 0.43 | 0.42 | 0.45 | 0.44 | 0.49 | 0.47 |
| MECADOX | 1 | 1 | 1 | 1 | 1 | 1 |
| Lys | 0.3 | 0.3 | 0.3 | 0.3 | 0.31 | 0.31 |
| Thr | 0.17 | 0.17 | 0.17 | 0.17 | 0.18 | 0.18 |
| MHA | 0 | 0.03 | 0 | 0.04 | 0 | 0.05 |
| DL-Met | 0.17 | 0 | 0.18 | 0 | 0.2 | 0 |
| Salt | 0.3 | 0.3 | 0.3 | 0.3 | 0.3 | 0.3 |
| CuSO$_4$ | 0.1 | 0.1 | 0.1 | 0.1 | 0.1 | 0.1 |
| ZnO | 0 | 0 | 0 | 0 | 0 | 0 |
| Vitamin | 0.25 | 0.25 | 0.25 | 0.25 | 0.25 | 0.25 |
| Mineral | 0.15 | 0.15 | 0.15 | 0.15 | 0.15 | 0.15 |
|  | 100 | 100 | 100 | 100 | 100 | 100 |

TABLE 5

Phase II Diet Formulations.

| Ingredient (lb/ton) | 2.5% Lactose | | 5% Lactose | | 10% Lactose | |
|---|---|---|---|---|---|---|
| | 0 DA | 0.5% DA | 0 DA | 0.5% DA | 0 DA | 0.5% DA |
| Corn | 1125.7 | 1117.8 | 1067.4 | 1059.4 | 950.9 | 942.8 |
| SBM | 600 | 600 | 600 | 600 | 600 | 600 |
| DAIRYLAC-80 | 62.5 | 62.5 | 125 | 125 | 250 | 250 |
| ACTIVATE DA | 0 | 10 | 0 | 10 | 0 | 10 |
| Fishmeal | 80 | 80 | 80 | 80 | 80 | 80 |
| SDPP | 0 | 0 | 0 | 0 | 0 | 0 |
| CWG | 47.52 | 48.5 | 44.63 | 45.72 | 38.9 | 40.15 |
| Dical | 26.79 | 26.8 | 24.79 | 24.8 | 20.78 | 20.8 |
| Lime | 8.68 | 8.49 | 9.06 | 8.81 | 9.82 | 9.46 |
| MECADOX | 20 | 20 | 20 | 20 | 20 | 20 |
| Lys | 6.01 | 6.04 | 6.06 | 6.08 | 6.15 | 6.17 |
| Thr | 3.32 | 3.34 | 3.4 | 3.42 | 3.57 | 3.59 |
| MHA | | 0.55 | 0 | 0.73 | 0 | 1.07 |
| DL-Met | 3.48 | 0 | 3.62 | 0 | 3.91 | 0 |
| Salt | 6 | 6 | 6 | 6 | 6 | 6 |
| CuSO$_4$ | 2 | 2 | 2 | 2 | 2 | 2 |
| ZnO | 0 | 0 | 0 | 0 | 0 | 0 |
| Vitamin | 5 | 5 | 5 | 5 | 5 | 5 |
| Mineral | 3 | 3 | 3 | 3 | 3 | 3 |
| | 2000 | 2000 | 2000 | 2000 | 2000 | 2000 |

TABLE 6

Phase II Diet Calculated Analyses.

| | 2.5% Lactose | | 5% Lactose | | 10% Lactose | |
|---|---|---|---|---|---|---|
| | 0 DA | 0.5% DA | 0 DA | 0.5% DA | 0 DA | 0.5% DA |
| ME, kcal/kg | 3400 | 3400 | 3400 | 3400 | 3400 | 3400 |
| CP, % | 21.9 | 21.9 | 21.8 | 21.8 | 21.6 | 21.7 |
| Ca, % | 0.8 | 0.8 | 0.8 | 0.8 | 0.8 | 0.8 |
| P, % AV | 0.45 | 0.45 | 0.45 | 0.45 | 0.45 | 0.45 |
| Lys, Tot | 1.48 | 1.48 | 1.48 | 1.48 | 1.48 | 1.48 |
| Lys, TID | 1.35 | 1.35 | 1.35 | 1.35 | 1.35 | 1.35 |
| TID TSAA/Lys | 60 | 60 | 60 | 60 | 60 | 60 |
| TID Thr/Lys | 65 | 65 | 65 | 65 | 65 | 65 |
| TID Trp/Lys | 17 | 17 | 17 | 17 | 17 | 17 |
| TID Val/lys | 76 | 76 | 75.7 | 75.6 | 74.9 | 74.8 |
| TID Ile/Lys | 60 | 60 | 60 | 60 | 59.4 | 59.3 |

The animals were observed daily including weekends and holidays. Any abnormal observations or mortalities were recorded by pen with weight and date. The body weights of the pigs were collected initially and at the end of each phase. The feed intake was collected for each phase of growth. Feed offered was measured by weighing each amount of feed used for each pen. Feed refused was measured by weighing the amount of feed left in the feeder and any remainder that had previously been recorded as feed offered.

Data were analyzed by analysis of variance procedures appropriate for a randomized block design using the General Linear Models procedure of SAS. Differences of least squares means for treatments from control pigs were determined using a least square comparison.

b. Results

The results of the Phase I treatments suggest that lactose level or acidifying agent did not affect growth performance (FIG. 1A, P>0.30) and a decreasing level of lactose coincided with a decreased feed intake (FIG. 1B, lactose effect: P<0.01). Inclusion of the acidifying agent improved feed efficiency (i.e., the gain to feed ratio, or GF) (FIG. 1C, acid effect; P<0.05), regardless of the lactose level. Inclusion of the lowest level of lactose resulted in lower feed intake compared to the intermediate and high levels of lactose (FIG. 1B, 132 vs. 150 and 146 g/d; P<0.05), the differences in feed intake did not result in improved weight gains. The improvement in feed efficiency (0.695 vs. 0.654 GF; P=0.05), with inclusion of the acidifying agent suggests improvements in digestibility and alterations in the microflora of the gastrointestinal tract resulting in more nutrients available for animal growth.

Figure 2:
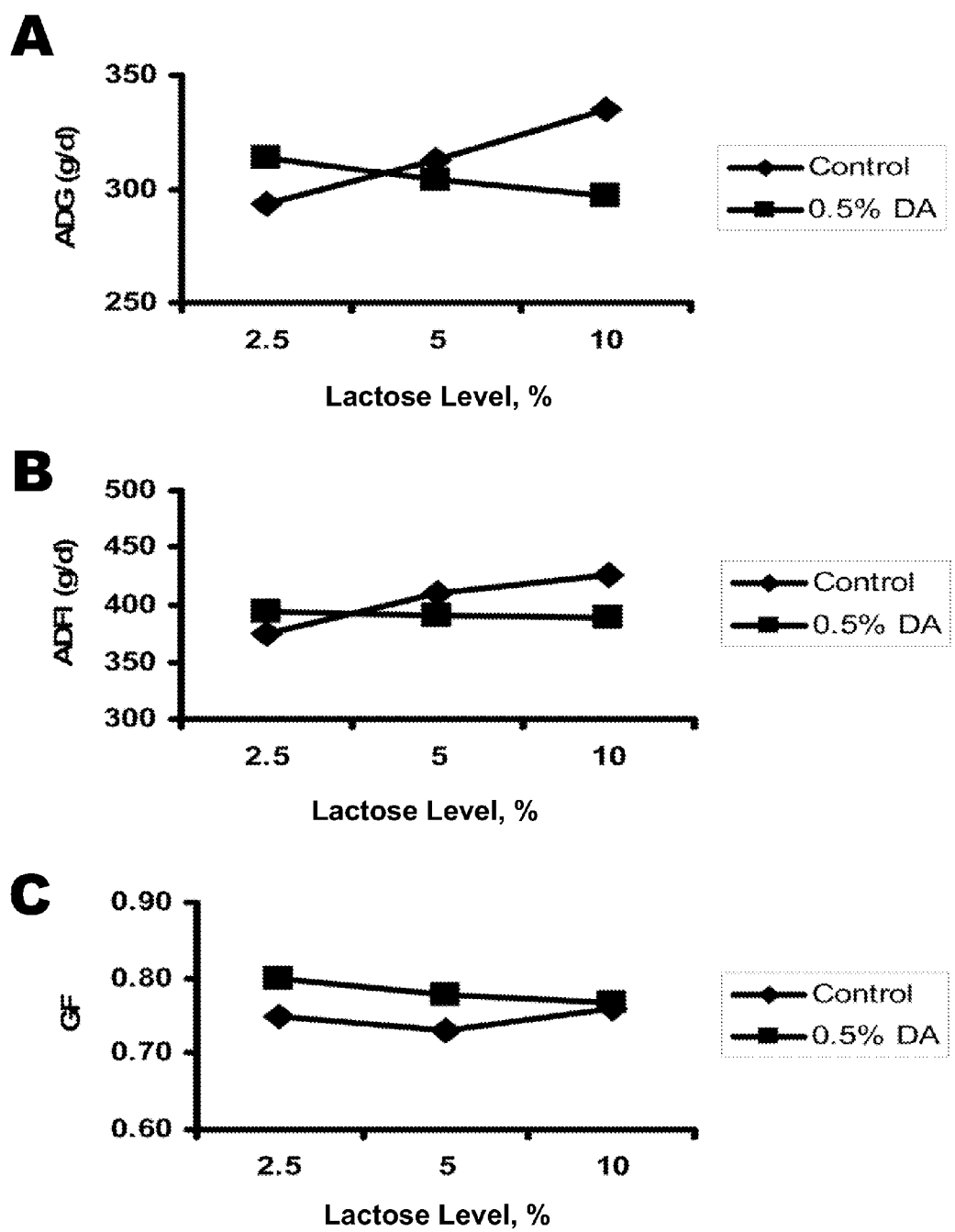
FIG. 2 graphically illustrates the effects of the level of lactose and an acidifying agent (DA) in nursery pig diets during Phase II (11 days to 21 days post weaning). Panel A presents the average daily weight gain (ADG) as a function of lactose level for the control and DA-treated groups. Panel B presents the average daily feed intake (ADFI) as a function of lactose level for the control and DA-treated groups. Panel C presents the gain to feed ratio (GF) as a function of lactose level for the control and DA-treated groups.

The results of the Phase II treatments, days 11 to 21 post weaning, suggest that the feed efficiency (GF) was not affected by the level of lactose, the presence of the acidifying agent, or the interaction (P>0.25). Also, inclusion of the acidifying agent resulted in similar levels of performance across all levels of lactose, but the growth rate was reduced in pigs that did not receive the acidifying agent with a decreasing level of lactose (FIG. 2A, lactose×acid; P<0.01). Pigs fed the acidifying agent tended to have lower feed consumptions (FIG. 2B, acid effect; P<0.10). Further, pigs fed the acidifying agent had similar levels of feed intake across all levels of lactose, whereas pigs had lower feed intake with a decreasing level of lactose in pigs that did not receive the acidifying agent (FIG. 2C, lactose effect; P<0.05, lactose×acid effect; P<0.02).

During this phase of growth (days 11-21 post weaning), lactose levels were reduced by 50% compared to the level fed during Phase I post weaning. The level of lactose did not affect the growth rate, but as the level of lactose increased, average daily feed intake (ADFI) increased (384 vs. 400 vs. 408 g/d; P<0.05), suggesting that beneficial effects on gut health increased with higher lactose levels. The level of lactose did not affect the feed efficiency (GF). Inclusion of the acidifying agent did not affect the growth rate or gain to feed ratio (GF), but tended to lower ADFI (391 vs. 403 g/d; P<0.10), particularly at the higher level of lactose. For example, the acidifying agent fed pigs had 8.7% less feed intake than pigs that did not receive the acidifying agent at the 10% level of lactose inclusion rate. However, at the low level of lactose inclusion rate (i.e., 2.5%), pigs fed the acidifying agent had 5.1% higher feed intake than pigs that did not receive the acidifying agent. These differences in responses to the acidifying agent by level of lactose resulted in a significant interaction (lactose×acid, P<0.02). Previous studies in examining the response of the acidifying agent in nursery pigs have been conducted in diets containing 20% and 10% lactose level for Phase I and II, respectively, has not shown reductions in feed intake with the acidifying agent.

Figure 3:
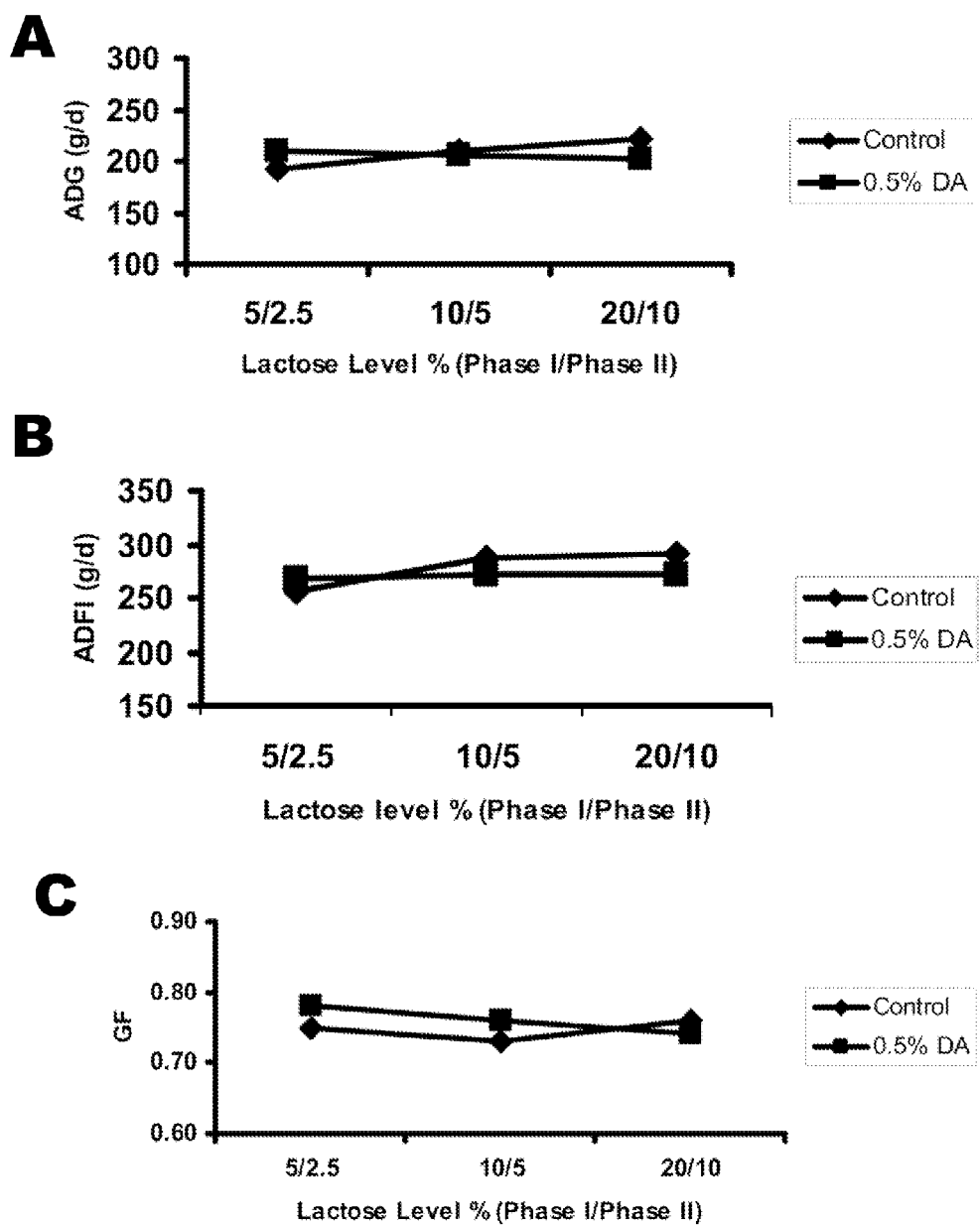
FIG. 3 graphically illustrates the overall effects of the level of lactose and an acidifying agent (DA) in nursery pig diets from 0 to 21 days post weaning. Panel A presents the average daily weight gain (ADG) as a function of lactose level for the control and DA-treated groups. Panel B presents the average daily feed intake (ADFI) as a function of lactose level for the control and DA-treated groups. Panel C presents the gain to feed ratio (GF) as a function of lactose level for the control and DA-treated groups.

Overall, from 0 to 21 days post weaning, the acidifying agent or lactose level did not affect the growth rate (P>0.19) or GF (P>0.13). Pigs fed the acidifying agent had a similar level of growth rate regardless of the level of lactose, whereas pigs that did not receive the acidifying agent had a decreased growth rate with a decreasing level of lactose (FIG. 3A, lactose×acid effect; P<0.01). Pigs fed lower levels of lactose had lower ADFI (FIG. 3B, lactose effect; P<0.01) compared to pigs fed higher levels of lactose. A greater feed intake reduction occurred in pigs fed low lactose and no acidifying agent (lactose×acid effect; P<0.04). Pig responses to different levels of lactose significantly interacted with the acidifying agent. The acidifying agent resulted in similar levels of growth rate and ADFI across all levels of lactose, but pigs that did not receive the acidifying agent had lower growth rate and ADFI with a decreasing level of lactose (FIG. 3B). Dietary lactose level and acidifying agent tended to interact in GF. Lowering the dietary lactose level tended to improve GF in pigs fed the acidifying agent, but tended to decrease GF in pigs not fed the acidifying agent (FIG. 3C, lactose×acid effect; P<0.09). The results are summarized in Table 7.

TABLE 7

Effect of Lactose Level and Acidifying Agent in Nursery Pig Diets.

| | 0 Acidifying Agent | | | 0.5% Acidifying Agent | | | | P value | | |
|---|---|---|---|---|---|---|---|---|---|---|
| | Lactose Level | | | Lactose Level | | | | | | Lact |
| | 5/2.5 | 10/5 | 20/10 | 5/2.5 | 10/5 | 20/10 | SEM | Lact | Acid | X acid |
| BW, kg | | | | | | | | | | |
| D 0 | 6.29 | 6.29 | 6.29 | 6.29 | 6.29 | 6.29 | 0.07 | 0.99 | 0.95 | 0.99 |
| D 10 | 7.17 | 7.28 | 7.29 | 7.27 | 7.31 | 7.27 | 0.09 | 0.69 | 0.61 | 0.80 |
| D 21 | $10.57^b$ | $10.82^{ab}$ | $11.06^a$ | $10.83^{ab}$ | $10.69^{ab}$ | $10.64^{ab}$ | 0.16 | 0.64 | 0.46 | 0.12 |
| D 0 to 10 | | | | | | | | | | |
| ADG, g/d | 86 | 99 | 99 | 97 | 101 | 98 | 6.1 | 0.33 | 0.38 | 0.61 |
| ADFI g/d | $130^b$ | $155^a$ | $147^{ab}$ | $134^b$ | $145^{ab}$ | $145^{ab}$ | 6.2 | 0.02 | 0.60 | 0.53 |
| GF | $0.658^{ab}$ | $0.638^b$ | $0.665^{ab}$ | $0.723^a$ | $0.698^{ab}$ | $0.664^{ab}$ | 0.025 | 0.53 | 0.05 | 0.36 |
| D 11 to 21 | | | | | | | | | | |
| ADG, g/d | $293^b$ | $313^{ab}$ | $335^a$ | $314^{ab}$ | $304^b$ | $297^b$ | 8.0 | 0.28 | 0.20 | 0.004 |
| ADFI, g/d | $374^c$ | $409^{ab}$ | $426^a$ | $393^{bc}$ | $390^{bc}$ | $389^{bc}$ | 9.1 | 0.04 | 0.10 | 0.02 |
| GF | 0.779 | 0.762 | 0.789 | 0.800 | 0.779 | 0.767 | 0.015 | 0.47 | 0.67 | 0.30 |
| D 0 to 21 | | | | | | | | | | |
| ADG g/d | $192^c$ | $210^{ab}$ | $221^a$ | $209^{ab}$ | $206^{abc}$ | $201^{bc}$ | 5.6 | 0.16 | 0.67 | 0.009 |
| ADFI g/d | $255^c$ | $287^{ab}$ | $292^a$ | $268^c$ | $272^{bc}$ | $271^{bc}$ | 6.4 | 0.01 | 0.17 | 0.03 |
| GF | $0.749^{ab}$ | $0.730^b$ | $0.758^{ab}$ | $0.781^a$ | $0.758^{ab}$ | $0.742^b$ | 0.011 | 0.20 | 0.13 | 0.09 |

$a,b,c$Means within a row with different superscripts differ (P < .05).

Pigs fed lower lactose diets had reduced performance, primarily through reduced feed intake. The inclusion of the acidifying agent appeared to abolish the depression in feed intake at low levels of dietary lactose. The mechanism for these effects could be through changes in the microbial population in the gastrointestinal tract. Higher levels of lactose would likely result in higher levels of *Lactobacilli* and limit growth of pathogenic bacteria. The antibacterial effects of the acidifying agent could depress growth of the pathogenic bacteria and maintain a vibrant population of beneficial bacteria.

In the above data, it appears that the acidifying agent suppressed performance in pigs fed higher lactose levels. Firstly, numerous previous studies conducted in the same research facility with similar diets (i.e. MECADOX® and 20% lactose levels) have not found these same results. A potential mechanism for this result could be that the acidifying agent and antibiotic suppressed the growth of beneficial bacteria, such as *Lactobacilli*, in the gastrointestinal tract and resulted in lower feed intake and growth performance.

In summary, reductions in growth performance and feed intake were ameliorated with the acidifying agent in pigs fed lower dietary lactose levels.

Example 2

Effect of a Blend of Gut Environmental Modifiers on Performance of Weaned Piglets The high cost of lactose feed ingredients in weaned piglet diets pushes producers to examine opportunities to reduce feed costs associated with high lactose nursery diets. Gut environmental modifiers include gut acidifying agents such as organic acids, immune enhancers such as microbial derived products, and *Lactobacillus* species or *Lactobacillus* species fermentation products have been shown to improve performance when fed to weaned animals. A blend of gut environmental modifiers is provided by ACIDOMATRIX® LOWLAC (Novus Intl.), which is hereinafter called the GEM blend. This GEM blend comprises organic acids (i.e., 2-hydroxy-4-methylthiobutanoic acid, fumaric acid, and benzoic acid as provided by ACTIVATE® STARTER DA), the yeast-derived immune stimulating agent mannanoligosaccharide (MOS), tri-butyrate ester of glycerol (i.e., BABY C4®; Silo Srl, Firenze, Italy), and 6-ethoxy-1,2-dihydro-2,2,4-trimethylquinoline (ethoxyquin) provided by AGRADO® (Novus Intl.).

The objective of the current trial was to determine the efficacy of the GEM blend on weaned piglet performance fed low lactose diets in comparison to the performance of piglets fed a control diet typically high in lactose, or low lactose diets containing only the organic acids component (i.e., ACTIVATE® STARTER DA) of the GEM blend, or a *Lactobacillus* species fermentation product.

a. Animals and Measurements

Approximately 840 pigs (TR4xC22, PIC Intl.) were weaned at about 19 days of age and blocked by weight and sex to pens of about 25 pigs/pen, with n=6 pens/treatment. The animals were observed daily including weekends and holidays. Any abnormal observations or mortalities were recorded by pen with weight and date. Body weight of pigs was collected at the start of the trial (day 0) and at the end of each phase (days 10, 21, and 42 post weaning), and feed consumption was measured daily. Feed offered was measured by weighing each amount of feed used for each pen. Feed refused was measured by weighing the amount of feed left in the feeder and any remainder that had previously been recorded as feed offered. Growth rate was calculated as average daily gain (ADG), daily feed intake was calculated as average daily feed intake (ADFI) and feed efficiency was calculated as the ratio of gain:feed (GF). Data were analyzed by analysis of variance procedures as a randomized complete block design using the General Linear Models procedure of SAS.

b. Diets and Treatment Groups

The animals were subjected to a 3-phase feeding regimen from days 0 to 10 (Phase I), from days 11 to 21 (Phase II), and from days 22 to 42 (Phase III) post weaning. Treatments were administered only for Phase I and II and followed a typical post weaning diet of decreasing lactose levels in each phase. All pigs received a standard Phase III diet without lactose. Composition and analysis of the experimental diets used in each phase are shown in Tables 8 to 13. Components altered among treatments are highlighted in italics. Treatment 1 was the positive control diet, which contained 20% and 10% lactose for Phase I and Phase II, respectively. Treatment 2 was a low lactose diet, which contained 5% and 2.5% lactose for Phase I and Phase II, respectively. All experimental treatments were conducted in low lactose diets. Treatment 3 comprised organic acids alone, treatment 4 comprised the GEM blend at high concentration in Phase I and II diets; treatment 5 comprised the GEM blend at high concentration in Phase I and lower concentration in Phase II; treatment 6 comprised the GEM blend at high concentration in Phase I and II diets with additional amounts of the butyrated glycerol (butyrate) component of the blend; and treatment 7 comprised a *Lactobacillus* species fermentation product. The seven treatment groups were as follows:

1. Positive control diet containing 20% lactose (Phase I) or 10% lactose (phase II)
2. Low lactose (negative control) diet containing 5% lactose (Phase I) or 2.5% lactose (Phase II)
3. Treatment 2+organic acids
4. Treatment 2+GEM blend at 6.25 kg/ton
5. Treatment 2+GEM blend at 6.25 kg/ton (Phase I) or 4.375 kg (Phase II)
6. Treatment 2+GEM blend at 6.25 kg/ton+0.7 kg of butyrate
7. Treatment 2+*Lactobacillus* product at 0.91 kg/ton Energy density was adjusted in all diets to about 3,352 kcal metabolizable energy (ME) per kg by increasing the percentage of corn in the low lactose diets. Also, during the third phase, there was no lactose in the diets, and distillers dried grains with solubles (DDGS) was included at 10% of the diet to reflect current or near-future industry standard diets. All diets were supplemented with the enteric antibiotic carbodox (i.e., MECADOX®). Methionine was from MHA (DL-methionine hydroxyl analog) in diets supplemented with organic acids or the GEM blend, and from DL-Met in the other diets. In all diets, lactose was from dried whey and DAIRYLAC-80®. The *Lactobacillus* species fermentation product was provided by CULBAC® (Culbac Products Inc, Kasota, Minn.).

TABLE 8

Composition of Phase I Experimental Diets.

| Ingredient* (%) | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| *Corn* | *40.28* | *57.88* | *57.55* | *57.47* | *57.47* | *57.39* | *57.78* |
| SBM (soy bean meal) | 15 | 15 | 15 | 15 | 15 | 15 | 15 |
| *DAIRYLAC-80 ®* | *16.5* | *4.12* | *4.12* | *4.12* | *4.12* | *4.12* | *4.12* |
| *Dried whey* | *10* | *2.5* | *2.5* | *2.5* | *2.5* | *2.5* | *2.5* |
| SDPP (spray-dried pig plasma) | 3 | 3 | 3 | 3 | 3 | 3 | 3 |
| CWG (choice white grease) | 2.9 | 3.75 | 3.75 | 3.75 | 3.75 | 3.75 | 3.75 |
| Fishmeal | 6 | 6 | 6 | 6 | 6 | 6 | 6 |
| Poultry meal | 3 | 4 | 4 | 4 | 4 | 4 | 4 |
| Limestone | 0.4 | 0.27 | 0.25 | 0.14 | 0.14 | 0.14 | 0.27 |

TABLE 8-continued

Composition of Phase I Experimental Diets.

| Ingredient* (%) | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| Dical (calcium source) | 0.02 | 0.61 | 0.61 | 0.61 | 0.61 | 0.61 | 0.61 |
| Enteric antibiotic | 1 | 1 | 1 | 1 | 1 | 1 | 1 |
| Lys | 0.34 | 0.35 | 0.35 | 0.35 | 0.35 | 0.35 | 0.35 |
| MHA | 0 | 0 | 0.06 | 0.06 | 0.06 | 0.06 | 0 |
| DL-Met | 0.24 | 0.21 | 0 | 0 | 0 | 0 | 21 |
| Thr | 0.17 | 0.16 | 0.16 | 0.16 | 0.16 | 0.16 | 0.16 |
| Salt | 0.4 | 0.4 | 0.4 | 0.4 | 0.4 | 0.4 | 0.4 |
| Vitamins | 0.25 | 0.25 | 0.25 | 0.25 | 0.25 | 0.25 | 0.25 |
| Minerals | 0.15 | 0.15 | 0.15 | 0.15 | 0.15 | 0.15 | 0.15 |
| Zinc oxide | 0.25 | 0.25 | 0.25 | 0.25 | 0.25 | 0.25 | 0.25 |
| CuSO$_4$ | 0.1 | 0.1 | 0.1 | 0.1 | 0.1 | 0.1 | 0.1 |
| Organic acids | 0 | 0 | 0.5 | 0 | 0 | 0 | 0 |
| GEM blend | 0 | 0 | 0 | 0.69 | 0.69 | 0.69 | 0 |
| Butyrate | 0 | 0 | 0 | 0 | 0 | 0.077 | 0 |
| Lactobacillus product | 0 | 0 | 0 | 0 | 0 | 0 | 0.1 |
| Total | 100.0 | 100.0 | 100.0 | 100.0 | 100.0 | 100.0 | 100.0 |

*Ingredients altered among treatments are highlighted in italics.

TABLE 9

Calculated Analyses of Phase I Experimental Diets.

| | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| ME kcal/kg | 3371 | 3362 | 3359 | 3344 | 3344 | 3344 | 3344 |
| CP, % | 21.36 | 22.0 | 22.1 | 22.1 | 22.1 | 22.1 | 22.1 |
| Ca, % | 0.8 | 0.8 | 0.8 | 0.8 | 0.8 | 0.8 | 0.8 |
| P, % AV | 0.45 | 0.45 | 0.45 | 0.45 | 0.45 | 0.45 | 0.45 |
| Lys, tot % | 1.54 | 1.55 | 1.55 | 1.55 | 1.55 | 1.55 | 1.55 |
| Lys, TID % | 1.4 | 1.4 | 1.4 | 1.4 | 1.4 | 1.4 | 1.4 |
| TSAA/Lys | 60 | 60 | 60 | 60 | 60 | 60 | 60 |
| Thr/Lys | 65 | 65 | 65 | 65 | 65 | 65 | 65 |
| Trp/Lys | 15 | 14.9 | 14.9 | 14.9 | 14.9 | 14.9 | 14.9 |

TABLE 10

Composition of Phase II Experimental Diets.

| Ingredient* (%) | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| Corn | 48.47 | 57.41 | 57.06 | 56.98 | 57.13 | 56.9 | 57.31 |
| SBM (soy bean meal) | 25 | 25 | 25 | 25 | 25 | 25 | 25 |
| DAIRYLAC-80 ® | 8.25 | 2.06 | 2.06 | 2.06 | 2.06 | 2.06 | 2.06 |
| Dried whey | 5 | 1.25 | 1.25 | 1.25 | 1.25 | 1.25 | 1.25 |
| SDPP | 0 | 0 | 0 | 0 | 0 | 0 | 0 |
| CWG | 3.1 | 3.6 | 3.6 | 3.6 | 3.6 | 3.6 | 3.6 |

TABLE 10-continued

Composition of Phase II Experimental Diets.

| Ingredient* (%) | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| Fishmeal | 3 | 3 | 3 | 3 | 3 | 3 | 3 |
| Limestone | 0.26 | 0.21 | 0.19 | 0.08 | 0.09 | 0.08 | 0.21 |
| Dical | 1.18 | 1.49 | 1.49 | 1.49 | 1.49 | 1.49 | 1.49 |
| Enteric antibiotic | 1 | 1 | 1 | 1 | 1 | 1 | 1 |
| Lys | 0.36 | 0.37 | 0.38 | 0.38 | 0.38 | 0.38 | 0.37 |
| MHA | 0 | 0 | 0.06 | 0.06 | 0.11 | 0.06 | 0 |
| DL-Met | 0.24 | 0.21 | 0 | 0 | 0 | 0 | 0.21 |
| Thr | 0.16 | 0.16 | 0.16 | 0.16 | 0.16 | 0.16 | 0.16 |
| Salt | 0.4 | 0.4 | 0.4 | 0.4 | 0.4 | 0.4 | 0.4 |
| CuSO4 | 0.1 | 0.1 | 0.1 | 0.1 | 0.1 | 0.1 | 0.1 |
| Vitamins | 0.25 | 0.25 | 0.25 | 0.25 | 0.25 | 0.25 | 0.25 |
| Minerals | 0.15 | 0.15 | 0.15 | 0.15 | 0.15 | 0.15 | 0.15 |
| *Organic acids* | *0* | *0* | *0.5* | *0* | *0* | *0* | *0* |
| *GEM blend* | *0* | *0* | *0* | *0.69* | *0.48* | *0.69* | *0* |
| *Butyrate* | *0* | *0* | *0* | *0* | *0* | *0.077* | *0* |
| *Lactobacillus product* | *0* | *0* | *0* | *0* | *0* | *0* | *0.1* |
| Total | 100.0 | 100.0 | 100.0 | 100.0 | 100.0 | 100.0 | 100.0 |

*Ingredients altered among treatments are highlighted in italics.

TABLE 11

Calculated Analyses of Phase II Experimental Diets.

| | 1 Positive Control | 2 Negative Control | 3 Organic acids | 4 GEM blend, Full | 5 GEM blend, Reduced | 6 GEM blend + Butyrate | 7 Lactobacillus product |
|---|---|---|---|---|---|---|---|
| ME kcal/kg | 3334 | 3340 | 3337 | 3322 | 3326 | 3322 | 3340 |
| CP, % | 21.76 | 21.9 | 22 | 22 | 22 | 22 | 22 |
| Ca, % | 0.8 | 0.8 | 0.8 | 0.8 | 0.8 | 0.8 | 0.8 |
| P, % AV | 0.45 | 0.45 | 0.45 | 0.45 | 0.45 | 0.45 | 0.45 |
| Lys, tot % | 1.49 | 1.49 | 1.49 | 1.49 | 1.49 | 1.49 | 1.49 |
| Lys, TID % | 1.35 | 1.35 | 1.35 | 1.35 | 1.35 | 1.35 | 1.35 |
| TSAA/Lys | 60 | 60 | 60 | 60 | 60 | 60 | 60 |
| Thr/Lys | 65 | 65 | 65 | 65 | 65 | 65 | 65 |
| Trp/Lys | 15 | 14.9 | 14.9 | 14.9 | 14.9 | 14.9 | 14.9 |

TABLE 12

Composition of Phase III Experimental Diet.

| Ingredient | % |
|---|---|
| Corn | 52.88 |
| SBM | 30.3 |
| DDGS | 10 |
| CWG | 3 |
| Limestone | 0.725 |
| Dical | 1.3 |
| Enteric antibiotic | 0.5 |
| Lys | 0.25 |
| MHA | 0.09 |
| Thr | 0.05 |
| Salt | 0.4 |
| CuSO$_4$ | 0.1 |
| Vitamins | 0.25 |
| Minerals | 0.15 |
| Total | 100.0 |

TABLE 13

Calculated Analysis of Phase III Experimental Diet.

| Item | Level |
|---|---|
| ME kcal/kg | 3390 |
| CP, % | 21.9 |
| Ca, % | 0.7 |

TABLE 13-continued

Calculated Analysis of Phase III Experimental Diet.

| Item | Level |
|---|---|
| P, % AV | 0.32 |
| Lys, tot % | 1.34 |
| Lys, TID % | 1.2 |
| TSAA/Lys | 60 |
| Thr/Lys | 65 |
| Trp/Lys | 16.3 | c. Results

The results are summarized in Table 14. Bodyweight was not significantly affected by dietary treatment during any period. In addition, for the entire nursery period (0 to 42 days), treatment did not affect any parameter measured ($P>0.10$)

The phase I period (from 0 to 10 days post weaning) is the most critical transition phase for weaned piglets where their diets are transitioned from the liquid high lactose milk of the sow to a solid diet lower in lactose. Lactose is generally added at high amounts during this phase to ease that transition. This is evident in the results of this trial where growth rate and daily feed intake from 0 to 10 days post weaning were significantly higher ($P<0.05$) in the pigs receiving the positive control high lactose than the low lactose diets. In this study, feed efficiency was not affected by dietary treatment.

For the phase II period (from 11 to 21 days post weaning), during which treatments were also administered, growth rate was not affected by dietary treatment. However, pigs receiving the positive control high lactose diet ate significantly more feed than the negative control pigs ($P<0.05$). Pigs fed the organic acids alone, GEM blend (full or reduced dose), or the *Lactobacillus* product had levels of feed intake that were similar to that of the positive control high lactose group. Pigs fed the positive and negative control diets and diets containing organic acids alone, and the GEM blend had similar feed efficiency. However, feed efficiency of pigs fed the *Lactobacillus* product was significantly higher than pigs fed the positive control high lactose diet ($P<0.05$).

For the phase III period (from 22 to 42 days post weaning), no treatment was administered, and feed intake or growth were not affected by dietary treatment implemented in the first two phases of the study (from 0 to 21 days post weaning). However, pigs fed the full dose of the GEM blend had higher feed efficiency than pigs fed the *Lactobacillus* product.

For the combined Phases I and II, during which the experimental diets were administered, pigs fed the positive control high lactose diet had greater growth rate and feed intake than pigs fed the negative control diet ($P<0.05$). Significantly, pigs fed organic acids alone, GEM blend (full or reduced dose), or the *Lactobacillus* product had growth rates similar to the positive control diet ($P>0.10$). The supplementation of the GEM blend with additional butyrate resulted in feed intake levels similar to the negative control diet and lower than the positive control diet. Pigs fed the *Lactobacillus* product had the highest feed efficiency of any treatment and was significantly higher than the full dose GEM blend ($P<0.05$), but was similar to the positive control diet ($P>0.10$).

TABLE 14

Effect of Dietary Treatment on Performance of Piglets.

| | Treatment | | | | | | |
|---|---|---|---|---|---|---|---|
| | 1 Positive Control | 2 Negative Control | 3 Organic Acids | 4 GEM blend, Full | 5 GEM blend, Reduced | 6 GEM blend + Butyrate | 7 Lacto product |
| BW, kg | | | | | | | |
| d 0 | 5.92 | 5.92 | 5.92 | 5.90 | 5.92 | 5.91 | 5.91 |
| d 10 | 7.77 | 7.45 | 7.43 | 7.50 | 7.48 | 7.43 | 7.54 |
| d 21 | 11.72 | 11.00 | 11.28 | 11.37 | 11.31 | 11.24 | 11.56 |
| d 42 | 21.22 | 20.07 | 20.43 | 20.94 | 20.52 | 20.68 | 20.60 |
| 0 to 10 days | | | | | | | |
| ADG, g/d | $183^a$ | $153^b$ | $150^b$ | $160^b$ | $157^b$ | $152^b$ | $160^b$ |
| ADFI, g/d | $205^a$ | $177^b$ | $175^b$ | $185^b$ | $183^b$ | $174^b$ | $183^b$ |
| GF | 0.890 | 0.867 | 0.849 | 0.866 | 0.853 | 0.869 | 0.872 |
| 11 to 21 days | | | | | | | |
| ADG, g/d | 359 | 319 | 336 | 348 | 347 | 341 | 361 |
| ADFI, g/d | $454^a$ | $395^b$ | $416^{ab}$ | $437^{ab}$ | $409^{ab}$ | $405^{ab}$ | $422^{ab}$ |
| GF | $0.789^b$ | $0.809^{ab}$ | $0.806^{ab}$ | $0.793^{ab}$ | $0.845^{ab}$ | $0.842^{ab}$ | $0.856^a$ |
| 22 to 42 days | | | | | | | |
| ADG, g/d | 555 | 533 | 533 | 559 | 536 | 551 | 531 |
| ADFI, g/d | 806 | 780 | 772 | 793 | 777 | 795 | 789 |
| GF | $0.690^{ab}$ | $0.684^{ab}$ | $0.690^{ab}$ | $0.706^a$ | $0.690^{ab}$ | $0.693^{ab}$ | $0.672^b$ |
| 0 to 21 days | | | | | | | |
| ADG, g/d | $275^a$ | $240^b$ | $246^{ab}$ | $258^{ab}$ | $256^{ab}$ | $250^{ab}$ | $264^{ab}$ |
| ADFI, g/d | $335^a$ | $291^b$ | $300^{ab}$ | $316^{ab}$ | $301^{ab}$ | $294^b$ | $307^{ab}$ |
| GF | $0.818^{ab}$ | $0.825^{ab}$ | $0.819^{ab}$ | $0.813^b$ | $0.849^{ab}$ | $0.849^{ab}$ | $0.862^a$ |
| 0 to 42 days | | | | | | | |
| ADG, g/d | 400 | 370 | 371 | 391 | 380 | 383 | 382 |
| ADFI, g/d | 545 | 509 | 506 | 528 | 512 | 515 | 521 |
| GF | 0.734 | 0.729 | 0.734 | 0.742 | 0.742 | 0.743 | 0.735 |

Treatments with the same superscripts (letters) are not significantly different.

Taken together, these results suggest that, even though pig performance was highest when fed high lactose, the performance loss with low lactose diets can be attenuated when some of these additives are used. This is especially evident from the data in Phase II, or the combined Phases I and II, in which pigs fed the GEM blend had the best performance among treatments. Moreover, the performance of the group fed the GEM blend was not significantly different than the positive control piglets fed the high lactose diets.

Example 3

Effect of a Blend of Gut Environmental Modifiers on Performance of Nursery Pig Diets Containing Low Lactose and Refined Carbohydrate Sources Early post weaning pig diets contain nearly 20% lactose, an expensive but essential component of their diets. In this experiment, dextrose, an alternate carbohydrate source was tested as a possible replacement for dietary lactose when fed to weaned piglets with or without the GEM blend (i.e., ACI-DOMATRIX® LOWLAC) described in Example 2 above. The specific objective of the current trial was to evaluate the interaction of alternate disaccharide carbohydrate sources and the GEM blend in weaned pig diets.

a. Animals and Measurements

Approximately 1050 piglets (TR4xC22, PIC Intl.) were weaned at about 19 days of age and blocked by weight and sex to pens of about 25 pigs/pen, with n=6 pens/treatment. The body weights of the pigs were collected initially (day 0) and at the end of each phase (days 7, 21, and 42 post weaning). Growth rate was calculated as average daily gain (ADG), daily feed intake was calculated as average daily feed intake (ADFI) and feed efficiency was calculated as the ratio of gain:feed (GF). Data were analyzed by analysis of variance procedures appropriate for a randomized block design using the General Linear Models procedure of SAS.

b. Diets and Treatment Groups

The animals were subjected to a 3-phase feeding regimen from days 0 to 7 (Phase I), from days 8 to 21 (Phase II), and from days 22 to 42 (Phase III) days post weaning. Treatments followed a typical post weaning diet of decreasing lactose or an alternate disaccharide in Phases I and II. The alternate disaccharide treatments were administered only during Phase I and II. Lactose replaced was from whey permeate, and the alternate CHO was a hydrolyzed sugar, predominantly dextrose. All diets were supplemented with the enteric antibiotic MECADOX®. The GEM blend was used at 6.25 kg/ton when applicable.

Piglets were assigned to one of 7 treatments. Treatment 1 was the positive control diet, which comprised the typical post weaning diets of 20% and 10% lactose in Phase I and II, respectively. Treatment 2 was the negative control diet, which comprised the low lactose levels of 5% and 2.5% in Phase I and II, respectively. Treatment 3 was a low lactose diet, which comprised 10% and 5% lactose respectively, supplemented with the GEM blend. Treatments 5-7 all comprised 20% and 10% disaccharide levels in Phase I and II, respectively, similar to the positive control treatment, but with different amounts of lactose being replaced by dextrose. Piglets that received the GEM blend during Phases I and II were fed a mix organic acids (i.e., ACTIVATE® DA) during Phase III. The seven treatment groups are summarized in Table 15 showing the total amount of disaccharide in each diet and the relative amount of disaccharide from lactose or dextrose. The seven treatments for each phase are as follows:

Phase I (0 to 7 Days)
1. Positive control diet containing 20% lactose.
2. Negative control diet containing 5% lactose.
3. Low lactose diet with 10% lactose+GEM blend.
4. A 50:50 disaccharide mix with 10% lactose and 10% dextrose+GEM blend.
5. A 25:75 disaccharide mix with 5% lactose and 15% dextrose+GEM blend.
6. A 50:50 disaccharide mix with 10% lactose and 10% dextrose.
7. A 50:50 disaccharide mix with 10% lactose and 10% dextrose+GEM blend.

Phase II (8 to 21 Days)
1. Positive control diet containing 10% lactose.
2. Negative control diet containing 2.5% lactose.
3. Low lactose diet with 5% lactose+GEM blend.
4. A 25:75 disaccharide mix with 2.5% lactose and 7.5% dextrose+GEM blend.
5. A 25:75 disaccharide mix with 2.5% lactose and 7.5% dextrose+GEM blend.
6. A 50:50 disaccharide mix with 5% lactose and 5% dextrose.
7. A 50:50 disaccharide mix with 5% lactose and 5% dextrose+GEM blend.

Phase III (22 to 42 days)
1. A control Phase III diet for treatments 1, 2, and 6.
2. The Phase III diet+organic acids for treatments 3, 4, 5, and 7.

TABLE 15

Relative Amounts of Disaccharides in Phase I and II Diets.

| | Treatments | | | | | | |
|---|---|---|---|---|---|---|---|
| | 1 Positive Con | 2 Negative Con | 3 Low lact Program + GEM | 4 50:50, 25:75 Lact:Dex + GEM | 5 25:75 Lact:Dex + GEM | 6 50:50 Lact:Dex | 7 Low lact 50:50 Lact:Dex + GEM |
| | Phase I (0 to 7 days) | | | | | | |
| Disaccharide Level, % | 20 | 5 | 10 | 20 | 20 | 20 | 20 |
| Lactose, % | 20 | 5 | 10 | 10 | 5 | 10 | 10 |
| Dextrose, % | 0 | 0 | 0 | 10 | 15 | 10 | 10 |
| | Phase II (7 to 21 days) | | | | | | |
| Dissaccharide Level, % | 10 | 2.5 | 5 | 10 | 10 | 10 | 10 |

TABLE 15-continued

Relative Amounts of Disaccharides in Phase I and II Diets.

| | Treatments | | | | | | |
|---|---|---|---|---|---|---|---|
| | 1 Positive Con | 2 Negative Con | 3 Low lact Program + GEM | 4 50:50, 25:75 Lact:Dex + GEM | 5 25:75 Lact:Dex + GEM | 6 50:50 Lact:Dex | 7 Low lact 50:50 Lact:Dex + GEM |
| Lactose, % | 10 | 2.5 | 5 | 2.5 | 2.5 | 5 | 5 |
| Dextrose, % | 0 | 0 | 0 | 7.5 | 7.5 | 5 | 5 | c. Results

Results of the various treatments in Phases I and II are summarized in Table 16. No differences in bodyweight were detected during any portion of the trial.

During the critical Phase I period (0 to 7 days post weaning), similar growth rates and daily feed intakes were detected between treatments 1, 4, 6, and 7. All these treatments contained at least 20% disaccharide, with at least half of the disaccharide being lactose. Conversely, diets containing less than 20% disaccharide levels, such as treatment 3, which contained only 10% disaccharide (all from lactose), or diets that contained less than 10% lactose, such as treatment 5, which contained 20% disaccharide levels but only 5% lactose, showed lower growth rates and feed intakes. Addition of the GEM blend improved performance in the pigs fed 20% disaccharide since pigs in treatment 4 gained faster (P<0.05) than either the negative control or pigs fed 10% lactose and the GEM blend (i.e., treatment 3). Feed efficiency was lower (P<0.05) for the negative control pigs fed only 5% lactose and pigs in treatment 3 fed only 10% disaccharides with the GEM blend than for positive control pigs and pigs in treatment 4 that were fed 20% disaccharides.

During phase II (8 to 21 days post weaning) or the combined Phases I and II (0 to 21 days post weaning), growth rates and feed intake were not significantly different between treatments (P>0.1). Treatments without the GEM blend (positive control, negative control, or treatment 6) had lower feed efficiency than the treatments with the GEM blend, and a higher (P<0.05) feed efficiency than the positive control pigs.

TABLE 16

Effect of CHO Source and GEM Blend on Early Nursery Performance.

| | Treatment | | | | | | |
|---|---|---|---|---|---|---|---|
| | 1 Positive Con | 2 Negative Con | 3 Low lact Program + GEM | 4 50:50, 25:75 Lact:Dex + GEM | 5 25:75 Lact:Dex + GEM | 6 50:50 Lact:Dex | 7 Low lact 50:50 Lact:Dex + GEM |
| BW, kg | | | | | | | |
| d 0 | 6.16 | 6.17 | 6.15 | 6.16 | 6.15 | 6.15 | 6.17 |
| d 7 | 7.39 | 6.97 | 7.07 | 7.33 | 7.11 | 7.14 | 7.18 |
| d 21 | 12.27 | 11.73 | 11.88 | 12.15 | 11.41 | 12.33 | 12.14 |
| d 42 | 25.23 | 24.62 | 24.48 | 24.88 | 24.41 | 25.48 | 24.66 |
| 0 to 7 d | | | | | | | |
| ADG, g/d | $175^a$ | $115^c$ | $131^{bc}$ | $167^{ab}$ | $136^{bc}$ | $140^{abc}$ | $145^{abc}$ |
| ADFI, g/d | $208^a$ | $168^c$ | $181^{bc}$ | $203^{ab}$ | $173^{bc}$ | $193^{abc}$ | $182^{abc}$ |
| GF | $0.847^a$ | $0.671^c$ | $0.721^{bc}$ | $0.819^{ab}$ | $0.789^{abc}$ | $0.728^{abc}$ | $0.790^{abc}$ |
| 8 to 21 d | | | | | | | |
| ADG, g/d | 337 | 317 | 334 | 330 | 325 | 357 | 345 |
| ADFI, g/d | 459 | 405 | 412 | 424 | 406 | 460 | 430 |
| GF | $0.736^b$ | $0.786^a$ | $0.810^a$ | $0.780^a$ | $0.799^a$ | $0.775^a$ | $0.801^a$ |
| 0 to 21 d | | | | | | | |
| ADG, g/d | 282 | 247 | 266 | 274 | 274 | 283 | 277 |
| ADFI, g/d | 374 | 323 | 334 | 348 | 339 | 369 | 346 |
| GF | $0.756^c$ | $0.767^{bc}$ | $0.793^{ab}$ | $0.788^{abc}$ | $0.805^a$ | $0.766^{bc}$ | $0.799^{ab}$ |
| 22 to 42 d | | | | | | | |
| ADG, g/d | 613 | 602 | 595 | 600 | 591 | 616 | 592 |
| ADFI, g/d | 963 | 958 | 944 | 935 | 935 | 990 | 943 |
| GF | 0.637 | 0.629 | 0.630 | 0.643 | 0.632 | 0.622 | 0.628 |
| 0 to 42 d | | | | | | | |
| ADG, g/d | 445 | 418 | 427 | 433 | 431 | 445 | 432 |
| ADFI, g/d | 664 | 629 | 633 | 634 | 635 | 672 | 640 |
| GF | $0.671^{ab}$ | $0.665^b$ | $0.674^{ab}$ | $0.684^a$ | $0.678^{ab}$ | $0.663^b$ | $0.674^{ab}$ |

Treatments with the same superscripts (letters) are not significantly different.

Results of the various treatments in Phase III are summarized in Table 17. During Phase III (22 to 42 days post weaning), there were no differences in growth rate, ADFI, or GF between treatments. For the combined phases I, II, and III (0 to 42 days post weaning), there were no differences in growth rates or feed intake between treatments. Feed efficiency was highest for pigs in treatment 4 fed the GEM blend at 20% and 10% disaccharide during Phases I and II, respectively, compared to the negative control pigs.

TABLE 17

Effect of Organic Acids in Late Nursery Performance.

| Item | Control | Organic acids (0.15%) |
|---|---|---|
| BW, kg | | |
| d 21 | 12.11 ± 0.398 | 11.92 ± 0.352 |
| d 42 | 25.11 ± 0.573 | 24.61 ± 0.496 |
| 22 to 42 d | | |
| ADG, g/d | 610 ± 9.4 | 594 ± 8.1 |
| ADFI, g/d | 971 ± 16.6 | 939 ± 14.4 |
| GF | 0.629 ± 0.004 | 0.633 ± 0.003 |

Combined, these results suggest that altering carbohydrate source from lactose via dextrose and providing the GEM blend when carbohydrate source was altered resulted in similar level of performance to a typical diet containing 20% lactose. During Phase III no differences in performance were detected between adding organic acids and control.

Example 4

Effects of Organic Trace Minerals And Antibiotics on Performance of a Blend of Gut Environmental Modifiers in Nursery Pigs Fed Low Lactose Diets Lactose is the major carbohydrate found in milk and is the main source of energy in suckling pigs. To allow for a smoother transition to other forms of dietary carbohydrates such as starch-based ingredients found in grains, early weaning diets generally are enriched with lactose, an expensive ingredient. It is desirable to identify less expensive alternatives that may optimize performance parameters of piglets fed low lactose diets. The objective of the present trial was to determine the efficacy of the GEM blend (i.e., ACIDOMATRIX® LOWLAC, described above in Example 2) when supplemented with organic trace minerals (OTMs) (i.e., HMTBA-Zn, HMTBA-Cu, and HMTBA-Mn as provided by MINTREX-P®, Novus Intl.), an enteric antibiotic, or a respiratory antibiotic in early weaning low lactose diets. The specific objectives of this study were:
  1. Determine if the GEM blend improved nursery pig performance in low lactose diets.
  2. Determine if OTMs improved nursery pig performance in low lactose diets supplemented with the GEM blend.
  3. Determine if different antibiotics improved nursery pig performance in low lactose diets supplemented with the GEM blend.
  a. Animals and Measurements
  Forty-two pens of pigs with about 20-25 pigs/pen blocked by weight were used. Pig body weights were collected initially (day 0) and at the end of each phase (days 7 and 21 post weaning). Feed consumption was measured from days 0-7 (Phase I) and from days 8-21 (Phase II) post weaning. Growth rate was calculated as average daily gain (ADG), daily feed intake was calculated as average daily feed intake (ADFI) and feed efficiency was calculated as the ratio of gain:feed (GF).
  b. Diets and Treatment Groups
  The animals were subjected to a 2-phase feeding regimen representative of typical post weaning diets where the amount of lactose is gradually decreased in phases. Phase I was from day 0 to 7 post weaning and Phase II was from day 8 to 21 post weaning. Composition and analysis of the experimental diets used in Phase I are described in Tables 18 and 19, respectively. Composition and analysis of the experimental diets used in Phase II are described in Tables 20 and 21, respectively. Diets in treatments 1 and 6 contained the high lactose levels of 20% and 10% in Phase I and II, respectively. All other treatments had diets containing the low lactose levels of 5% and 2.5% in Phase I and II, respectively. Antibiotic, GEM blend and OTM treatments during the two phases were as follows:

Phase I (0 to 7 Days):
  1. High lactose (20%)+enteric antibiotic.
  2. Low lactose (5%)+enteric antibiotic.
  3. Low lactose (5%)+enteric antibiotic+GEM blend.
  4. Low lactose (5%)+enteric antibiotic+OTM.
  5. Low lactose (5%)+enteric antibiotic+OTM+GEM blend.
  6. High lactose (20%)+respiratory antibiotic.
  7. Low lactose (5%)+respiratory antibody+OTM+GEM blend.

Phase II (8 to 21 Days)
  1. High lactose (10%)+enteric antibiotic.
  2. Low lactose (2.5%)+enteric antibiotic.
  3. Low lactose (2.5%)+enteric antibiotic+GEM blend.
  4. Low lactose (2.5%)+enteric antibiotic+OTM.
  5. Low lactose (2.5%)+enteric antibiotic+OTM+GEM blend.
  6. High lactose (10%)+respiratory antibiotic.
  7. Low lactose (2.5%)+respiratory antibiotic+OTM+GEM blend.

Energy density was adjusted in all diets to about 3,230 kcal metabolizable energy (ME) per kg by increasing the percentage of corn in low lactose diets. All Phase I diets contained a high concentration of the inorganic trace minerals Zn at 2000 ppm and Cu at 150 ppm. All Phase II diets contained a high concentration of the inorganic trace mineral Cu at 150 ppm. The GEM blend was from ACIDOMATRIX® LOWLAC and was used at 6.25 kg/ton when appropriate. The organic trace minerals (OTMs) were from MINTREX-P® and were used at 0.1% when appropriate. The enteric antibiotic was MECADOX® and was used at 5.5 g/kg. The respiratory antibiotic was from a combination of chlortetracycline (CTC) used at 110 g/kg and DENAGARD® (Novartis Animal Health, Basel, Switzerland) used at 22 g/kg. In all diets, lactose was from DAIRYLAC-80®.

TABLE 18

Composition of Phase I Experimental Diets.

| Ingredient* | 1 High lactose + enteric % | 2 Low lactose + enteric % | 3 Low lactose + enteric + GEM % | 4 Low lactose + enteric + OTM % | 5 Low lactose + enteric + GEM + OTM % | 6 High lactose + resp. % | 7 Low lactose + resp. + GEM + OTM % |
|---|---|---|---|---|---|---|---|
| *Corn* | *37.84* | *55.91* | *55.55* | *55.84* | *55.44* | *38.27* | *55.87* |
| SBM | 15.00 | 15.00 | 15.00 | 15.00 | 15.00 | 15.00 | 15.00 |
| *DAIRYLAC-80 ®* | *24.40* | *6.10* | *6.10* | *6.10* | *6.10* | *24.40* | *6.10* |
| Poultry meal | 8.22 | 7.76 | 7.78 | 7.76 | 7.79 | 8.22 | 7.79 |
| Fishmeal | 5.00 | 5.00 | 5.00 | 5.00 | 5.00 | 5.00 | 5.00 |
| SDPP | 3.00 | 3.00 | 3.00 | 3.00 | 3.00 | 3.00 | 3.00 |
| CWG | 3.50 | 3.50 | 3.50 | 3.50 | 3.50 | 3.50 | 3.50 |
| MonoCal | 0.00 | 0.47 | 0.47 | 0.47 | 0.47 | 0.00 | 0.47 |
| *Lime* | *0.19* | *0.27* | *0.02* | *0.20* | *0.02* | *0.19* | *0.02* |
| *Enteric antibiotic* | *1.00* | *1.00* | *1.00* | *1.00* | *1.00* | *0.00* | *0.00* |
| *Respiratory antibiotic (CTC)* | *0.00* | *0.00* | *0.00* | *0.00* | *0.00* | *0.40* | *0.40* |
| *Respiratory antibiotic (DENAGARD ®)* | *0.00* | *0.00* | *0.00* | *0.00* | *0.00* | *0.18* | *0.17* |
| Lys | 0.30 | 0.30 | 0.30 | 0.30 | 0.30 | 0.30 | 0.30 |
| Thr | 0.15 | 0.13 | 0.13 | 0.13 | 0.13 | 0.15 | 0.13 |
| MHA | 0.00 | 0.00 | 0.08 | 0.21 | 0.08 | 0.00 | 0.08 |
| DL-Met | 0.22 | 0.18 | 0.00 | 0.00 | 0.00 | 0.22 | 0.00 |
| Salt | 0.40 | 0.40 | 0.40 | 0.40 | 0.40 | 0.40 | 0.40 |
| $CuSO_4$ | 0.10 | 0.10 | 0.10 | 0.10 | 0.10 | 0.10 | 0.10 |
| ZnO | 0.28 | 0.28 | 0.27 | 0.27 | 0.27 | 0.28 | 0.27 |
| Vitamin | 0.25 | 0.25 | 0.25 | 0.25 | 0.25 | 0.25 | 0.25 |
| Mineral | 0.15 | 0.15 | 0.15 | 0.15 | 0.15 | 0.15 | 0.15 |
| *OTM* | *0.00* | *0.00* | *0.00* | *0.10* | *0.10* | *0.00* | *0.10* |
| *GEM blend* | *0.00* | *0.00* | *0.69* | *0.00* | *0.69* | *0.00* | *0.69* |
| KCl | 0.00 | 0.20 | 0.20 | 0.20 | 0.20 | 0.00 | 0.20 |
| Total | 100.00 | 100.00 | 100.00 | 100.00 | 100.00 | 100.00 | 100.00 |

*Ingredients altered among treatments are highlighted in italics.

TABLE 19

Calculated Analyses of Phase I Experimental Diets.

| | 1 High lactose + enteric | 2 Low lactose + enteric | 3 Low lactose + enteric + GEM | 4 Low lactose + enteric + OTM | 5 Low lactose + enteric + GEM + OTM | 6 High lactose + resp. | 7 Low lactose + resp. + GEM + OTM |
|---|---|---|---|---|---|---|---|
| ME, kcal/kg | 3260 | 3228 | 3215 | 3228 | 3212 | 3260 | 3212 |
| CP, % | 23.3 | 23.6 | 23.7 | 23.7 | 23.7 | 23.3 | 23.7 |
| Ca, % | 0.8 | 0.8 | 0.8 | 0.8 | 0.8 | 0.8 | 0.8 |
| P, % AV | 0.46 | 0.45 | 0.45 | 0.45 | 0.45 | 0.46 | 0.45 |
| Lys, Tot | 1.56 | 1.56 | 1.56 | 1.56 | 1.56 | 1.56 | 1.56 |
| Lys, TID | 1.4 | 1.4 | 1.4 | 1.4 | 1.4 | 1.4 | 1.4 |
| TID TSAA/Lys | 60 | 60 | 60 | 60 | 60 | 60 | 60 |
| Thr/Lys | 65 | 65 | 65 | 65 | 65 | 65 | 65 |
| Trp/Lys | 15.6 | 15.5 | 15.5 | 15.5 | 15.5 | 15.6 | 15.5 |
| Valine/Lys | 63.9 | 65.9 | 65.8 | 65.9 | 65.8 | 63.9 | 65.8 |
| Na | 0.61 | 0.4 | 0.4 | 0.4 | 0.4 | 0.61 | 0.4 |
| K | 1.13 | 0.85 | 0.85 | 0.85 | 0.85 | 1.13 | 0.85 |

TABLE 20

Composition of Phase II Experimental Diets.

| | Treatment | | | | | | |
|---|---|---|---|---|---|---|---|
| Ingredient* | 1 High lactose + enteric % | 2 Low lactose + enteric % | 3 Low lactose + enteric + GEM % | 4 Low lactose + enteric + OTM % | 5 Low lactose + enteric + GEM + OTM % | 6 High lactose + resp. % | 7 Low lactose + resp. + GEM + OTM % |
|---|---|---|---|---|---|---|---|
| Corn | 46.36 | 55.23 | 54.86 | 55.15 | 54.75 | 46.78 | 55.18 |
| SBM | 25.00 | 25.00 | 25.00 | 25.00 | 25.00 | 25.00 | 25.00 |
| DAIRYLAC-80 ® | 12.20 | 3.10 | 3.10 | 3.10 | 3.10 | 12.20 | 3.10 |
| Poultry meal | 6.14 | 5.92 | 5.95 | 5.93 | 5.95 | 6.14 | 5.95 |
| Fishmeal | 3.00 | 3.00 | 3.00 | 3.00 | 3.00 | 3.00 | 3.00 |
| SDPP | 0.00 | 0.00 | 0.00 | 0.00 | 0.00 | 0.00 | 0.00 |
| CWG | 3.50 | 3.50 | 3.50 | 3.50 | 3.50 | 3.50 | 3.50 |
| MonoCal | 0.91 | 1.17 | 1.17 | 1.17 | 1.17 | 0.92 | 1.17 |
| Lime | 0.36 | 0.38 | 0.14 | 0.32 | 0.14 | 0.36 | 0.14 |
| Enteric antibiotic | 1.00 | 1.00 | 1.00 | 1.00 | 1.00 | 0.00 | 0.00 |
| Respiratory antibiotic (CTC) | 0.00 | 0.00 | 0.00 | 0.00 | 0.00 | 0.40 | 0.40 |
| Respiratory antibiotic (DENAGARD ®) | 0.00 | 0.00 | 0.00 | 0.00 | 0.00 | 0.18 | 0.18 |
| Lys | 0.30 | 0.30 | 0.30 | 0.30 | 0.30 | 0.30 | 0.30 |
| Thr | 0.14 | 0.13 | 0.13 | 0.13 | 0.13 | 0.14 | 0.13 |
| MHA | 0.00 | 0.00 | 0.07 | 0.20 | 0.07 | 0.00 | 0.07 |
| DL-Met | 0.19 | 0.17 | 0.00 | 0.00 | 0.00 | 0.19 | 0.00 |
| Salt | 0.40 | 0.40 | 0.40 | 0.40 | 0.40 | 0.40 | 0.40 |
| $CuSO_4$ | 0.10 | 0.10 | 0.10 | 0.10 | 0.10 | 0.10 | 0.10 |
| ZnO | 0.00 | 0.00 | 0.00 | 0.00 | 0.00 | 0.00 | 0.00 |
| Vitamin | 0.25 | 0.25 | 0.25 | 0.25 | 0.25 | 0.25 | 0.25 |
| Mineral | 0.15 | 0.15 | 0.15 | 0.15 | 0.15 | 0.15 | 0.15 |
| OTM | 0.00 | 0.00 | 0.00 | 0.10 | 0.10 | 0.00 | 0.10 |
| GEM blend | 0.00 | 0.00 | 0.69 | 0.00 | 0.69 | 0.00 | 0.69 |
| KCl | 0.00 | 0.20 | 0.20 | 0.20 | 0.20 | 0.00 | 0.20 |
| Total | 100.00 | 100.00 | 100.00 | 100.00 | 100.00 | 100.00 | 100.00 |

*Ingredients altered among treatments are highlighted in italics.

TABLE 21

Calculated Analyses of Phase II Experimental Diets.

| | Treatments | | | | | | |
|---|---|---|---|---|---|---|---|
| | 1 High lactose + enteric | 2 Low lactose + enteric | 3 Low lactose + enteric + GEM | 4 Low lactose + enteric + OTM | 5 Low lactose + enteric + GEM + OTM | 6 High lactose + resp. | 7 Low lactose + resp. + GEM + OTM |
|---|---|---|---|---|---|---|---|
| ME, kcal/kg | 3261 | 3240 | 3228 | 3240 | 3224 | 3261 | 3224 |
| CP, % | 23.2 | 23.3 | 23.4 | 23.4 | 23.4 | 23.2 | 23.4 |
| Ca, % | 0.8 | 0.8 | 0.8 | 0.8 | 0.8 | 0.8 | 0.8 |
| P, % AV | 0.45 | 0.45 | 0.45 | 0.45 | 0.45 | 0.45 | 0.45 |
| Lys, Tot | 1.5 | 1.5 | 1.5 | 1.5 | 1.5 | 1.5 | 1.5 |
| Lys, TID | 1.35 | 1.35 | 1.35 | 1.35 | 1.35 | 1.35 | 1.35 |
| TID TSAA/Lys | 60 | 60 | 60 | 60 | 60 | 60 | 60 |
| Thr/Lys | 65 | 65 | 65 | 65 | 65 | 65 | 65 |
| Trp/Lys | 15.7 | 15.6 | 15.6 | 15.6 | 15.6 | 15.7 | 15.6 |
| Valine/Lys | 64.1 | 65.1 | 65.1 | 65.1 | 65.1 | 64.1 | 65.1 |
| Na | 0.37 | 0.26 | 0.26 | 0.26 | 0.26 | 0.37 | 0.26 |
| K | 1.03 | 0.94 | 0.94 | 0.94 | 0.94 | 1.03 | 0.94 | c. Results

Effect of OTMs on performance of the GEM blend. The results are presented in Table 22. Overall, supplemental OTM did not improve the performance of pigs fed the GEM blend. However, from 0 to 7 days post weaning, pigs fed supplemental OTM had improved feed efficiency compared to pigs fed no additional minerals. This response could have been generated by increased the level and/or source of mineral. Also, in the present trial, minimal responses to the GEM blend were found in low lactose diets.

TABLE 22

Effect of the GEM Blend and OTMs on Piglet Performance.

| | Treatment | | | | | Probability | | |
|---|---|---|---|---|---|---|---|---|
| | 2 | 4 | 3 | 5 | | | | GEM × |
| OTM | Neg control | | GEM | | | | | |
| (MINTREX ®-P) | − | + | − | + | SEM | GEM | OTM | OTM |
| Item Bodyweight (kg) | | | | | | | | |
| d 0 | 5.47 | 5.47 | 5.46 | 5.48 | 0.05 | 0.97 | 0.92 | 0.87 |
| d 7 | 6.69 | 6.65 | 6.61 | 6.66 | 0.07 | 0.62 | 0.91 | 0.51 |
| d 21 | 11.52 | 11.32 | 11.19 | 11.29 | 0.20 | 0.38 | 0.82 | 0.47 |
| d 0 to 7 | | | | | | | | |
| ADG, g/d | 174 | 169 | 164 | 169 | 6.4 | 0.46 | 1.0 | 0.41 |
| ADFI, g/d | 185 | 172 | 180 | 177 | 6.7 | 0.97 | 0.26 | 0.50 |
| GF | 0.944 | 0.978 | 0.908 | 0.958 | 0.021 | 0.20 | 0.06 | 0.71 |
| d 8 to 21 | | | | | | | | |
| ADG, g/d | 329 | 320 | 311 | 322 | 11.4 | 0.50 | 0.92 | 0.42 |
| ADFI, g/d | 409 | 399 | 395 | 408 | 12.2 | 0.87 | 0.88 | 0.37 |
| GF | 0.804 | 0.801 | 0.784 | 0.789 | 0.012 | 0.19 | 0.91 | 0.75 |
| d 0 to 21 | | | | | | | | |
| ADG, g/d | 276 | 269 | 261 | 271 | 8.8 | 0.46 | 0.88 | 0.35 |
| ADFI, g/d | 332 | 322 | 321 | 331 | 9.5 | 0.91 | 0.97 | 0.33 |
| GF | 0.830 | 0.834 | 0.808 | 0.819 | 0.011 | 0.10 | 0.51 | 0.74 |

Effects of medication source on performance of the GEM blend. The results described below and summarized in Table 23, show that lactose level and/or addition of the GEM blend were affected by the source of medication.

During phase I (0 to 7 days post weaning), there was no difference in body weight, growth rate or feed efficiency between treatments. Pigs fed the respiratory antibiotic tended to have higher feed intakes than pigs fed the enteric antibiotic (194 vs. 179 g/d; P<0.07), regardless of lactose level.

The results were similar for Phase II (8-21 days post weaning) and the combined Phases I and II (0 to 21 days post weaning). Pigs fed enteric antibiotic had higher growth rates in high lactose diets, but lower growth rates when fed low lactose with the GEM blend compared to the respiratory antibiotic. Similarly, feed efficiency varied with the level of lactose and type of medication, with pigs fed high lactose having higher feed efficiency with the enteric antibiotic, but pigs fed low lactose and the GEM blend having higher feed efficiency with the respiratory antibiotic. Pigs fed the enteric antibiotic had higher feed efficiency than pigs fed the respiratory antibiotic in high lactose diets, but lower feed efficiency in low lactose diets containing the GEM blend. In Phase II, pigs fed high lactose diets tended to have higher feed intake than pigs fed low lactose and the GEM blend (442 vs 419 g/d; P<0.09).

TABLE 23

Effect of the GEM Blend and Medication Source on Piglet Performance.

| | Treatment | | | | | Probability | | |
|---|---|---|---|---|---|---|---|---|
| | 1 | 6 | 5 | 7 | | | | |
| | Pos control | | LowLac | | | | | |
| Medication | Enteric | Resp. | Enteric | Resp. | SEM | Lact | Med | Lact × Med |
| Body weight, kg | | | | | | | | |
| d 0 | 5.48 | 5.47 | 5.48 | 5.47 | 0.07 | 0.97 | 0.93 | 0.97 |
| d 7 | 6.69 | 6.78 | 6.66 | 6.82 | 0.10 | 0.95 | 0.22 | 0.71 |
| d 21 | 11.85$^x$ | 11.42$^{xy}$ | 11.29$^y$ | 11.76$^{xy}$ | 0.21 | 0.62 | 0.91 | 0.05 |
| d 0 to 7 | | | | | | | | |
| ADG, g/d | 174 | 188 | 169 | 192 | 11 | 0.99 | 0.10 | 0.65 |
| ADFI, g/d | 182$^{xy}$ | 196$^x$ | 177$^y$ | 191$^{xy}$ | 7 | 0.54 | 0.07 | 0.97 |
| GF | 0.958 | 0.958 | 0.958 | 1.001 | 0.037 | 0.58 | 0.57 | 0.58 |
| d 8 to 21 | | | | | | | | |
| ADG, g/d | 354$^a$ | 320$^b$ | 322$^b$ | 343$^{ab}$ | 10 | 0.66 | 0.52 | 0.01 |
| ADFI, g/d | 448$^a$ | 435$^{ab}$ | 408$^b$ | 430$^{ab}$ | 12 | 0.09 | 0.75 | 0.17 |
| GF | 0.789$^a$ | 0.737$^b$ | 0.789$^a$ | 0.800$^a$ | 0.012 | 0.02 | 0.09 | 0.02 |

TABLE 23-continued

Effect of the GEM Blend and Medication Source on Piglet Performance.

| | Treatment | | | | | | | |
|---|---|---|---|---|---|---|---|---|
| | 1 6 Pos control | | 5 7 LowLac | | | Probability | | |
| Medication | Enteric | Resp. | Enteric | Resp. | SEM | Lact | Med | Lact × Med |
| d 0 to 21 | | | | | | | | |
| ADG, g/d | 293$^x$ | 275$^{xy}$ | 271$^y$ | 292$^x$ | 8 | 0.75 | 0.84 | 0.03 |
| ADFI, g/d | 358 | 354 | 331 | 349 | 10 | 0.13 | 0.48 | 0.25 |
| GF | 0.819$^a$ | 0.779$^b$ | 0.819$^a$ | 0.837$^a$ | 0.008 | 0.003 | 0.19 | 0.003 |

Treatments with the same superscripts (letters) are not significantly different.

In summary, the GEM blend in low lactose diets had greater performance when medicated with the respiratory than with the enteric antibiotic. With the GEM blend providing adequate enteric control and the respiratory antibiotic providing respiratory control, the combination of both treatments provides more overall control of disease pressure, resulting in better performance.

Example 5

Effect of Energy Density And Organic Acids On Performance of Late Nursery Pigs

Meeting dietary energy requirements is difficult for swine producers due to ingredient availability and increasing cereal grain costs. Reducing diet costs by using lower quality (lower energy density) feeds must be accompanied by measures mitigating associated performance losses, such as performance enhancing feed additives. The objective of this trial was to evaluate the effect of a blend of organic acids containing HMTBA, benzoic acid, and fumaric acid (i.e., ACTIVATE® STARTER DA) in late nursery pigs fed diets with lower than ideal energy densities.

a. Animals and Measurements

Forty pens of pigs with about 20-25 pigs/pen were used. At 21 days post weaning, pigs were blocked by weight and sex, and pens were randomly assigned to a 2×2 factorial arrangement (n=10 pen/treatment) with feed energy density and levels of organic acids as factors for a period of 21 days. Data collection and measurements were as described in Example 2 above. Data were analyzed for the effects of energy density, organic acids, and their interaction.

b. Diets and Treatment Groups

Composition and analyses of diets used in this study are described in Tables 24 and 25 below. Diets were formulated to provide a similar level of nutrients other than energy. Treatments 1 and 2 comprised high energy diets without or with organic acids, respectively. Treatments 3 and 4 comprised low energy diets without or with organic acids, respectively. The treatments were as follows:

1. High energy density diet, no organic acids
2. High energy density diet+organic acids
3. Low energy density diet, no organic acids
4. Low energy density diet+organic acids The duration of the study was 21 days. Dietary energy densities were 3460 vs. 3285 kcal of metabolizable energy (ME)/kg. High energy diets contained corn, soy bean meal (SBM) and 4% choice white grease (CWG). Low energy density was achieved by decreasing the rate of dietary fat inclusion from 4% to 1% and including 10% wheat middlings. The organic acids were from ACTIVATE® STARTER DA used at 0.3%. All diets were supplemented with the enteric antibiotic MECADOX® used at the rate of 25 g/kg.

TABLE 24

Composition of Experimental Diets.

| | Treatment | | | | | | | |
|---|---|---|---|---|---|---|---|---|
| | 1 High Energy No organic acids | | 2 High Energy + organic acids | | 3 Low Energy No organic acids | | 4 Low Energy + organic acids | |
| Ingredient* | Lbs | % | Lbs | % | Lbs | % | Lbs | % |
| Corn | 1231.79 | 61.59 | 1227.54 | 61.38 | 1123.34 | 56.17 | 1119.02 | 55.95 |
| SBM | 600.78 | 30.04 | 601.09 | 30.05 | 571.5 | 28.58 | 571.81 | 28.59 |
| *CWG* | *80* | *4.00* | *80* | *4.00* | *20* | *1.00* | *20* | *1.00* |
| *Wheat Midds* | *0* | *0.00* | *0* | *0.00* | *200* | *10.00* | *200* | *10.00* |
| MonoCal | 28.18 | 1.41 | 28.18 | 1.41 | 25.52 | 1.28 | 25.53 | 1.28 |
| Lime | 18.95 | 0.95 | 18.45 | 0.92 | 19.75 | 0.99 | 19.37 | 0.97 |
| Enteric antibiotic | 10 | 0.50 | 10 | 0.50 | 10 | 0.50 | 10 | 0.50 |
| Lys | 6 | 0.30 | 6 | 0.30 | 6 | 0.30 | 6 | 0.30 |
| Thr | 2.16 | 0.11 | 2.16 | 0.11 | 2.07 | 0.10 | 2.07 | 0.10 |
| MHA | 0 | 0.00 | 1.57 | 0.08 | 0 | 0.00 | 1.2 | 0.06 |
| DL-Met | 3.14 | 0.16 | 0 | 0.00 | 2.82 | 0.14 | 0 | 0.00 |
| Salt | 10 | 0.50 | 10 | 0.50 | 10 | 0.50 | 10 | 0.50 |
| Vitamin | 6 | 0.30 | 6 | 0.30 | 6 | 0.30 | 6 | 0.30 |

TABLE 24-continued

Composition of Experimental Diets.

| | Treatment | | | | | | | |
|---|---|---|---|---|---|---|---|---|
| | 1 High Energy No organic acids | | 2 High Energy + organic acids | | 3 Low Energy No organic acids | | 4 Low Energy + organic acids | |
| Ingredient* | Lbs | % | Lbs | % | Lbs | % | Lbs | % |
| Mineral | 3 | 0.15 | 3 | 0.15 | 3 | 0.15 | 3 | 0.15 |
| *Organic acids* | *0* | *0.00* | *6* | *0.30* | *0* | *0.00* | *6* | *0.30* |
| Total | 2000.0 | 100.0 | 2000.0 | 100.0 | 2000.0 | 100.0 | 2000.0 | 100.0 |

*Ingredients altered among treatments are highlighted in italics.

TABLE 25

Calculated Analyses of Experimental Diets.

| | Treatment | | | |
|---|---|---|---|---|
| | 1 High Energy No organic acids | 2 High Energy + organic acids | 3 Low Energy No organic acids | 4 Low Energy + organic acids |
| ME, kcal/kg | 3465 | 3462 | 3287 | 3284 |
| CP, % | 20.1 | 20.2 | 20.6 | 20.7 |
| Ca, % | 0.7 | 0.7 | 0.7 | 0.7 |
| P, % AV | 0.32 | 0.32 | 0.32 | 0.32 |
| Lys, Tot | 1.33 | 1.33 | 1.33 | 1.34 |
| Lys, TID | 1.2 | 1.2 | 1.2 | 1.2 |
| TID TSAA/Lys | 60 | 60 | 60 | 60 |
| Thr/Lys | 65 | 65 | 65 | 65 |
| Trp/Lys | 16 | 16 | 16 | 16 |
| Valine/Lys | 65 | 65 | 62 | 61 | c. Results

Results are summarized in Table 26. Ending bodyweights, growth rates, or rates of feed intake were not different for high vs. low energy diets in treatments 1 and 3, respectively. High energy diets had 1.5% greater feed efficiency than low energy diets (0.652 vs. 0.635±0.003; P<0.01).

Addition of organic acids did not affect final bodyweights, growth rates, or feed intake in high or low energy diets. However, organic acids increased feed efficiency by 2.5% (0.651 vs. 0.635 GF; P<0.01) when added to low energy diets (treatments 3 and 4), but not to high energy diets (treatments 1 and 2).

These results show that organic acids abolish the reduction in feed efficiency associated with low energy diets. The improvement in GF was only found in low, but not in the high energy dense diet.

TABLE 26

Effect of Dietary Energy Density and Organic Acids in Late Nursery Pigs.

| | Treatment | | | | |
|---|---|---|---|---|---|
| | 1 | 2 | 3 | 4 | |
| | High Energy | | Low Energy | | |
| Organic acids | 0 | 0.3% | 0 | 0.3% | SEM |
| BW, kg | | | | | |
| d 21 | 11.55 | 11.54 | 11.55 | 11.53 | 0.48 |
| d 42 | 24.22 | 24.19 | 24.15 | 24.10 | 0.72 |
| ADG, g/d | 603 | 602 | 599 | 595 | 12 |
| ADFI, g/d | 926 | 919 | 944 | 915 | 21 |
| GF | $0.652^a$ | $0.655^a$ | $0.635^b$ | $0.651^a$ | 0.004 |

Treatments with the same superscripts (letters) are not significantly different.

Example 6

Effect of a Blend of Gut Environmental Modifiers On Performance of Nursery Pigs Fed Low Lactose Diets Lactose, the main source of energy in suckling pigs is beneficial for weaned piglet performance and gut health. To allow for a smoother transition to other forms of dietary carbohydrates such as starch-based ingredients found in grains, early weaning diets generally are enriched with lactose, an expensive ingredient. The high cost of lactose feed ingredients in weaned piglet diets, usually added at a rate of up to 20% of feed content, push producers to examine opportunities to reduce feed costs associated with high lactose nursery diets. In addition to the high price of lactose, swine producers are also faced with difficulties in meeting dietary energy requirements due to ingredient availability and increasing cereal grain costs.

Gut environmental modifiers and modifier blends such as ACIDOMATRIX® LOWLAC, described in Example 2, have the potential to mitigate the effects of reducing levels of lactose in early diets of weaned piglets. Previous trials with the GEM blend in low lactose diets of early-weaned piglets have demonstrated economic benefits, but numerically lower bodyweights at the end of the nursery, which is not acceptable to producers. The significant reduction of lactose levels fed to piglets in the critical first phase (i.e. 0 to 7 days post weaning), when lactose is critical to weaned piglet health and performance (see Examples 2, 3, and 4 supra), could have caused the decreased performance. An objective of the present trial was to investigate whether pig performance could be improved in Phase I with the ACIDOMATRIX® LOWLAC blend of gut environment modifiers (GEM) when lactose levels are not changed, and whether pig performance could be maintained in Phase II when lactose levels are reduced. The specific objectives of this study were:

1. Determine if the GEM blend improves performance in piglets fed low lactose diets in the middle weaning phase (Phase II).
2. Determine if the GEM blend is necessary in the early weaning phase (Phase I) to show improvements in piglets fed low lactose diets in the middle weaning phase (Phase II).

a. Animals, Treatment Groups, and Measurements

Approximately 480 weaned nursery pigs were blocked by bodyweight and sex at 20-25 pigs/pen, and pens were randomly assigned to one of four treatments. The treatments were as follows:

1. Positive control diet comprising 20% lactose (Phase I) or 10% lactose (Phase II).
2. Negative control diet comprising 20% lactose (Phase I) or 2.5% lactose (Phase II).
3. Treatment 2+GEM blend at 0.69% during Phase II.
4. Treatment 2+GEM blend at 0.69% during Phases I and II.

This study followed a regimen of diets for the three early phases post weaning: days 0-7 (Phase I), and days 8-24 (Phase II) post weaning. All diets followed a typical regimen of decreasing lactose concentration in diets administered in the two phases. All of the diets were supplemented with the enteric antibiotic MECADOX®. All of the Phase I diets contained Zn at 2000 ppm and Cu at 250 ppm. All of the Phase II diets contained Cu at 250 ppm.

Pig body weights were collected initially (day 0) and at the end of each phase (days 7 and 24 post weaning). Feed consumption was measured from days 0-7 (Phase I) and from days 8-24 (Phase II) post weaning. Growth rate was calculated as average daily gain (ADG), daily feed intake was calculated as average daily feed intake (ADFI) and feed efficiency was calculated as the ratio of gain:feed (GF). Fresh fecal samples were collected at day 10 from one pig per pen. The total number of coliform bacteria, *E. coli*, *Clostridium*, and lactic acid-producing bacteria were determined.

The pigs were challenged by a natural outbreak of hemolytic *E. coli* from 10 to 24 days of the study, resulting in a high rate of mortality. The treatment comprised including neomycin in the water.

b. Results

Treatments and results are summarized in Table 27. No differences in bodyweight were detected between treatments at any time point measured. For phase I (0-7 days post weaning), there were no differences in growth rates or feed intake between treatments. Feed efficiency tended to be higher in treatments 1 and 2 vs. treatment 3, even though there was no difference in the formulation of these diets in this phase.

For Phase II (8-24 days post weaning), pigs fed the GEM blend during both Phases I and II tended to have higher growth rates and feed intakes than the negative control pigs. Feed efficiency was higher in pigs fed the GEM blend than the positive control diet.

Overall, from 0 to 24 days post weaning, pigs fed the GEM blend during both Phases I and II tended to perform better than the negative control, and were comparable to positive control pigs. Mortality rates were numerically higher for the negative control diet compared to pigs fed the GEM blend or the positive control diet.

These results show that for optimal piglet performance, lactose content in Phase I diets should not be altered. However, since pigs consume very little amount of feed during the Phase I period of growth (i.e., maximum of 2 kg/pig) maintaining a premium feed at this stage should not affect the bottom line for the farmer and could still result in significant savings from significantly reducing lactose content in Phase II diets. No significant differences were detected between treatment groups for the number of total coliform bacteria, *E. coli*, *Clostridium*, and lactic acid-producing bacteria.

TABLE 27

GEM Blend and Lactose Content in Treatment Diets, and Their Effect on Piglet Performance During Phase II.

| | Phase I and II treatment | | | |
|---|---|---|---|---|
| | 1 Positive Control | 2 Negative Control | 3 GEM blend in Phase II only | 4 GEM blend in Phase I & II |
| Lactose (%) | | | | |
| Phase I | 20 | 20 | 20 | 20 |
| Phase II | 10 | 2.5 | 2.5 | 2.5 |
| GEM blend | | | | |
| Phase I | − | − | − | + |
| Phase II | − | − | + | + |
| Bodyweights, kg | | | | |
| d 0 | 6.21 | 6.20 | 6.21 | 6.21 |
| d 7 | 7.34 | 7.33 | 7.27 | 7.39 |
| d 24 | 12.73 | 12.48 | 12.46 | 12.91 |
| 0 to 7 days | | | | |
| ADG, g/d | 161 | 152 | 149 | 163 |
| ADFI, g/d | 167 | 158 | 165 | 170 |
| GF | $0.967^x$ | $0.967^x$ | $0.904^y$ | $0.954^{xy}$ |
| 8 to 24 days | | | | |
| ADG, g/d | $291^{xy}$ | $278^y$ | $294^{xy}$ | $309^x$ |
| ADFI, g/d | $416^a$ | $389^{ab}$ | $382^b$ | $404^{ab}$ |
| GF | $0.693^b$ | $0.706^{ab}$ | $0.766^a$ | $0.763^a$ |
| 0 to 24 days | | | | |
| ADG, g/d | $250^{xy}$ | $239^y$ | $250^{xy}$ | $264^x$ |
| ADFI, g/d | $338^x$ | $316^y$ | $317^y$ | $332^{xy}$ |
| GF | $0.736^b$ | $0.751^{ab}$ | $0.789^a$ | $0.794^a$ |
| Mortality, % | 6.4 | 13.5 | 7.2 | 8.0 |
| Off-test, % | 7.9 | 6.4 | 4.8 | 6.4 |
| Removal, total % | 14.3 | 19.9 | 11.9 | 14.3 |

Treatments with the same superscripts (letters) are not significantly different.
$^{a,b}$(P < 0.05)
$^{x,y}$(P < 0.10)

What is claimed is:

1. A method for transitioning a piglet from weaning to a grower/finisher diet by feeding the piglet a ration comprising a low percentage of fermentable carbohydrate, the method comprising replacing at least about 50% of fermentable carbohydrate in a piglet feed ration from about day 0 to about day 24 post weaning with a replacement dry composition comprising a low lactose diet containing less than 10% lactose for a piglet feed ration, the replacement dry composition comprising:

at least one acidifying agent, wherein the acidifying agent comprises at least one compound selected from the group consisting of 2-hydroxy-4-methylthiobutanoic acid (HMTBA), butyric acid, phosphoric acid, formic acid, acetic acid, propionic acid, butanoic acid, benzoic acid, lactic acid, malic acid, tartaric acid, mandelic acid, citric acid, fumaric acid, sorbic acid, boric acid, succinic acid, adipic acid, glycolic acid, and glutaric acid, at least one immune stimulating agent, wherein the immune stimulating agent comprises a peptidoglycan or comprises a yeast derived product selected from the group consisting of β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides, at least one antioxidant, and at least one tissue regeneration agent, the tissue regeneration agent being a polyol esterified to at least one carboxylic acid or substituted carboxylic acid having from three to twelve carbon atoms, the polyol selected from the group consisting of glycerol, erythritol, xylitol, sorbitol, maltitol, mannitol, and inulin, wherein the replacement of the fermentable carbohydrate does not substantially negatively impact the piglet in one or more selected from the group consisting of growth performance, feed efficiency, daily feed intake and bodyweight.

2. The method of claim 1, wherein the acidifying agent comprises of HMTBA, formic acid, butyric acid, fumaric acid, lactic acid, benzoic acid, phosphoric acid, propionic acid, sorbic acid, or citric acid.

3. The method of claim 1, wherein the acidifying agent comprises HMTBA, fumaric acid, and benzoic acid.

4. The method of claim 1, wherein the immune stimulating agent comprises mannan oligosaccharide.

5. The method of claim 1, wherein the immune stimulating agent comprises beta-glucans.

6. The method of claim 1, wherein the antioxidant comprises a mixture of 6-ethoxy-1,2-dihydro-2,2,4-trimethyliquinoline and tertiary butyl hydroquinone.

7. The method of claim 1, wherein the low lactose diet contains 5% lactose for a piglet feed ration.

8. The method of claim 1, wherein the low lactose diet contains 2.5% lactose for a piglet feed ration.

* * * * *